US012788223B2

(12) United States Patent
Zhang et al.

(10) Patent No.: US 12,788,223 B2
(45) Date of Patent: Nov. 10, 2026

(54) SCANNING FIBER ENDOSCOPE PROBES AND SCANNING FIBER ENDOSCOPES

(71) Applicant: HANG AN MEDTECH (HANGZHOU) CO., LTD., Hangzhou (CN)

(72) Inventors: Cheng Zhang, Hangzhou (CN); Mintao Ru, Hangzhou (CN); Baiming Shi, Hangzhou (CN)

(73) Assignee: HANG AN MEDTECH (HANGZHOU) CO., LTD., Hangzhou (CN)

( * ) Notice: Subject to any disclaimer, the term of this patent is extended or adjusted under 35 U.S.C. 154(b) by 244 days.

(21) Appl. No.: 18/681,051

(22) PCT Filed: Aug. 9, 2022

(86) PCT No.: PCT/CN2022/111076
§ 371 (c)(1),
(2) Date: Feb. 3, 2024

(87) PCT Pub. No.: WO2023/016438
PCT Pub. Date: Feb. 16, 2023

(65) Prior Publication Data

US 2024/0366071 A1 Nov. 7, 2024

(30) Foreign Application Priority Data

Aug. 10, 2021 (CN) ........................ 202110912064.9

(51) Int. Cl.
*A61B 1/00* (2006.01)

(52) U.S. Cl.
CPC ...... *A61B 1/00172* (2013.01); *A61B 1/00167* (2013.01)

(58) Field of Classification Search
CPC ............ A61B 1/00172; A61B 1/00167; A61B 1/00096; A61B 1/07; A61B 1/00
See application file for complete search history.

(56) References Cited

U.S. PATENT DOCUMENTS 4,913,142 A * 4/1990 Kittrell .................. G02B 6/241 606/7
6,364,257 B1 * 4/2002 Holder .................... F16L 3/237 248/74.1

(Continued)

FOREIGN PATENT DOCUMENTS

CN 101247753 A 8/2008
CN 104053394 A 9/2014

(Continued)

OTHER PUBLICATIONS

International Search Report in PCT/CN2022/111076 mailed on Nov. 2, 2022, 9 pages.

(Continued)

*Primary Examiner* — Anhtuan T Nguyen
*Assistant Examiner* — Shankar Raj Ghimire
(74) *Attorney, Agent, or Firm* — METIS IP LLC

(57) ABSTRACT

The embodiments of the present disclosure provide a scanning fiber endoscope probe and a scanning fiber endoscope. The scanning fiber endoscope probe includes: a scanning illumination optical path and an inner-layer fiber collecting array, wherein the scanning illumination optical path includes a lens set, and the scanning illumination optical path is configured to scan laser emitted by a light source to form an optical spot on a surface of a sample tissue and to form a field of view; and the inner-layer fiber collecting array is configured to collect and transmit a portion of (Continued)

detecting light scattered from or reflected by the sample tissue through the lens set to perform an imaging by a photoelectric detector.

18 Claims, 12 Drawing Sheets

(56) References Cited

U.S. PATENT DOCUMENTS

| | | | | | |
|---|---|---|---|---|---|
| 6,485,413 | B1* | 11/2002 | Boppart | G01N 21/4795 | 600/478 |
| 7,813,538 | B2* | 10/2010 | Carroll | A61B 1/041 | 382/128 |
| 8,096,943 | B2* | 1/2012 | Melville | A61B 1/07 | 600/149 |
| 8,932,209 | B2* | 1/2015 | Akui | A61B 1/00172 | 600/173 |
| 9,877,640 | B2* | 1/2018 | Okita | G02B 23/26 | |
| 10,025,087 | B2* | 7/2018 | Mori | G02B 26/103 | |
| 10,502,947 | B2* | 12/2019 | Hasegawa | A61B 1/00165 | |
| 2001/0055462 | A1* | 12/2001 | Seibel | A61B 1/00048 | 385/33 |
| 2005/0192480 | A1* | 9/2005 | Toriya | A61B 1/00167 | 600/128 |
| 2007/0015969 | A1* | 1/2007 | Feldman | A61B 5/0084 | 600/160 |
| 2007/0213618 | A1* | 9/2007 | Li | G01J 3/42 | 600/476 |
| 2008/0058629 | A1* | 3/2008 | Seibel | A61B 1/07 | 600/368 |
| 2008/0141947 | A1* | 6/2008 | Luo | A01K 15/025 | 119/707 |
| 2008/0165360 | A1* | 7/2008 | Johnston | A61B 5/0062 | 356/394 |
| 2008/0249369 | A1* | 10/2008 | Seibel | A61B 1/00183 | 600/182 |
| 2008/0262312 | A1* | 10/2008 | Carroll | A61B 1/00172 | 600/160 |
| 2008/0265178 | A1* | 10/2008 | Johnston | A61B 1/00006 | 250/492.1 |
| 2008/0306470 | A1* | 12/2008 | Friedman | A61B 1/0607 | 606/3 |
| 2009/0026888 | A1* | 1/2009 | Melville | A61B 1/00172 | 310/335 |
| 2009/0028407 | A1* | 1/2009 | Seibel | A61B 1/0627 | 382/131 |
| 2009/0092364 | A1* | 4/2009 | Johnston | A61B 1/00096 | 385/116 |
| 2009/0135280 | A1* | 5/2009 | Johnston | A61B 1/3132 | 348/262 |
| 2009/0177042 | A1* | 7/2009 | Johnston | A61B 5/0062 | 356/406 |
| 2009/0316116 | A1* | 12/2009 | Melville | H04N 9/3129 | 348/742 |
| 2010/0123775 | A1* | 5/2010 | Shibasaki | A61B 1/0638 | 348/E7.085 |
| 2010/0125167 | A1* | 5/2010 | Sugimoto | A61B 1/00167 | 600/109 |
| 2011/0037841 | A1* | 2/2011 | Shibasaki | A61B 1/07 | 348/E7.085 |
| 2014/0073950 | A1* | 3/2014 | Akui | A61B 1/0002 | 600/478 |
| 2014/0114131 | A1* | 4/2014 | Sakai | A61B 1/0011 | 600/182 |
| 2014/0296639 | A1* | 10/2014 | Sakai | A61B 1/00165 | 600/146 |
| 2015/0029570 | A1* | 1/2015 | Ito | G02B 23/24 | 359/198.1 |
| 2015/0313503 | A1* | 11/2015 | Seibel | A61B 5/065 | 600/103 |
| 2016/0150948 | A1* | 6/2016 | Shimamoto | A61B 1/00006 | 600/179 |
| 2017/0056064 | A1* | 3/2017 | Zergiebel | A61B 17/3474 | |
| 2017/0090185 | A1* | 3/2017 | Fujinuma | A61B 1/00006 | |
| 2017/0242239 | A1* | 8/2017 | Tsuruta | G02B 23/2469 | |
| 2017/0296037 | A1* | 10/2017 | Yoshino | A61B 1/0646 | |
| 2018/0003953 | A1* | 1/2018 | Fujiwara | A61B 1/00172 | |
| 2019/0004233 | A1* | 1/2019 | Shimamoto | G02B 23/24 | |
| 2019/0200867 | A1* | 7/2019 | Yokota | A61B 1/00172 | |
| 2019/0265459 | A1* | 8/2019 | Hirata | A61B 1/0669 | |
| 2024/0366071 | A1* | 11/2024 | Zhang | A61B 1/00096 | |

FOREIGN PATENT DOCUMENTS

| | | | |
|---|---|---|---|
| CN | 106662742 | A | 5/2017 |
| CN | 110353609 | A | 10/2019 |
| WO | 2020240015 | A2 | 12/2020 |

OTHER PUBLICATIONS

Written Opinion in PCT/CN2022/111076 mailed on Nov. 2, 2022, 8 pages.

* cited by examiner

Amended FIG. 8

SCANNING FIBER ENDOSCOPE PROBES AND SCANNING FIBER ENDOSCOPES

CROSS-REFERENCE TO RELATED APPLICATIONS

This application is a U.S. national stage under 35 U.S.C. § 371 of International Application No. PCT/CN2022/111076, filed on Aug. 9, 2022, which claims priority to Chinese application No. 202110912064.9, filed on Aug. 10, 2021, the entire contents of each of which are incorporated herein by reference.

TECHNICAL FIELD

The present disclosure relates to the field of optical endoscopy, in particular to scanning fiber endoscope probes and scanning fiber endoscopes.

BACKGROUND

With the rapid development of medical information technology, endoscopy is also gaining attention as a key medical device for collecting, analyzing information, and aiding treatment. An endoscope provides a doctor with an intuitive optical image of an interior of a human body, and has features of low damage and high resolution, and therefore the endoscope is widely used for observing and diagnosing lesions of tissues or organs such as a digestive tract, a reproductive tract, and a respiratory tract. The diameter and flexibility of the endoscope are crucial to endoscopic imaging technology, which determines a target imaging region that the endoscope can reach, a degree of discomfort to the user, and a degree of influence on the trauma of the tissue. Therefore, the endoscope with a tiny probe can flexibly penetrate deep into the living tissue to image the tissue and cells, thereby driving the medical endoscope to develop in a direction of the fiber, miniaturization, flexibility, and high-resolution.

The earliest endoscope uses a coherent fiber bundle (CFB) and is used in a clinical endoscopy model and examines the upper gastrointestinal tract. One end of the endoscope that is inserted into a body cavity of a patient is referred to as a distal end, and one end that is held by the user of the endoscope is referred to as a proximal end. This endoscope uses the CFB to guide light at the distal end and uses a charge-coupled device (CCD) or complementary metal-oxide-semiconductor (CMOS) detector at the proximal end for detection, due to its flexibility and small outer diameter, a digital camera chip, such as the CCD or the CMOS, contains a light-sensitive layer, in which silicon converts the light radiation into the electrical charge, ultimately an image is generated. The endoscope has become a routine examination in the gastroenterology department of a hospital.

With the development of semiconductor processes, a miniaturized camera chip is developed and placed on the tip of the endoscopic probe to become a new generation of chip-on-tip endoscopy (CTE). Since an optical signal is converted into an electrical signal directly at the tip of the probe, the CTE merely requires four wires to transmit the signal from the distal end to the proximal end of the probe and thus has the advantage of being soft and having a high count of pixels. However, there is a minimum upper limit on the pixel size of the CTE to obtain sufficient optical radiation energy, and the circuitry of CTE occupies additional space, which makes it difficult to further increase the count of pixels. For many cases that require high-resolution examination of relatively thin cavities in the human body, it is necessary to use an ultrafine micro high-resolution endoscope with small diameters, at this time the endoscopes based on image sensors or fiber bundles cannot be used due to their limitations such as size and resolution.

A Grating-based spectrally encoded endoscopy (SEE) is another technique that is easily miniaturized and flexible. The technique uses complex-color light and gratings to achieve reflectance measurements at a plurality of points in the sample in parallel in the direction of the grating dispersion. This parallel technique does not need to scan and therefore facilitates the miniaturization of the probe. The effective count of pixels in SEE depends on the spectral resolution of the grating, which breaks through the pixel density limit existing in CFB and CTE. However, the current grating-based SSE is unable to provide color images.

A scanning fiber endoscope (SFE) actively controls a fiber to swing and guide a laser beam to scan for color imaging through a driving mechanism, and the SFE has the features of small size, large visual field, and high resolution. Since an emergent optical spot at an end of a fiber cantilever in the SFE is extremely small, a large count of effective pixels can be allowed, and thus the SFE has a wide clinical application prospect. At the proximal end of the SFE, the three central wavelengths of red, green, and blue laser are combined into a coaxial beam by a beam combiner and transmitted to the distal end of the SFE by a single-mode fiber. A piezoelectric ceramic tube located at the tip of the probe holds one end of the single-mode fiber in place with a free fiber cantilever. Under a drive of an alternating voltage, the piezoelectric ceramic tube drives the single-mode fiber to oscillate. When the frequency of a drive voltage is set to a resonant frequency of the fiber cantilever, the end of the cantilever achieves a large lateral displacement to form a great field of view. The detecting light is collected and detected by a fixed large field of view collecting channel, and in the related technology, the collection amount of optical intensity signal of the detecting light is proportional to the imaging quality, and due to a limitation of an external size of the endoscope probe, an efficiency for collecting the light energy signal is not high, which affects the imaging quality of the scanning fiber endoscope.

Therefore, it is desirable to provide a new scanning fiber endoscope probe and a scanning fiber endoscope to improve the imaging quality of the endoscopy.

SUMMARY

According to some embodiments of the present disclosure, a scanning fiber endoscope probe is provided, the scanning fiber endoscope probe includes: a scanning illumination optical path and an inner-layer fiber collecting array; the scanning illumination optical path includes a lens set, and the scanning illumination optical path is configured to scan laser emitted by a light source to form an optical spot on a surface of a sample tissue and to form a field of view; and the inner-layer fiber collecting array is configured to collect and transmit a portion of detecting light scattered from or reflected by the sample tissue through the lens set to perform an imaging by a photoelectric detector.

In some embodiments, the scanning illumination optical path further includes a sleeve, the inner-layer fiber collecting array is fixed within a cavity of the sleeve.

In some embodiments, the inner-layer fiber collecting array is a tubular fiber array surrounded by at least two collecting fibers in a uniform arrangement.

In some embodiments, the scanning illumination optical path further includes: a vibrating component and a fixture; the vibrating component is disposed within a cavity of a sleeve and at a proximal end of the lens set; and the fixture fixes the vibrating component within the sleeve.

In some embodiments, the inner-layer fiber collecting array is located at the proximal end of the lens set and is disposed on an outer side of the vibrating component, and the fixture installs the inner-layer fiber collecting array between the sleeve and the vibrating component.

In some embodiments, the inner-layer fiber collecting array is located at the proximal end of the lens set and is disposed on an outer side of the vibrating component, and the inner-layer fiber collecting array is disposed on an outer side of the fixture.

In some embodiments, the fixture is a circular ring with an opening, one end of the opening of the circular ring is provided with a first buckle, another end of the opening of the circular ring is provided with a first slot, the first buckle is inserted into the first slot, and then the first buckle and the first slot are fixed relative to each other by using a first fixing member.

In some embodiments, the first buckle is in a ratchet-toothed shape, and the first slot is provided with a protrusion matching with the ratchet-toothed shape of the first buckle to enable unidirectional movement of the first buckle within the first slot.

In some embodiments, the fixture is divided into a first half-circular ring and a second half-circular ring, each of two ends of the first half-circular ring is provided with a second buckle, respectively, each of two ends of the second half-circular ring is provided with a second slot, respectively, the second buckle is inserted into the first slot, and then the second buckle and the second slot are fixed relative to each other by using a second fixing member.

In some embodiments, the second buckle is in the ratchet-toothed shape and the second slot is provided with a protrusion corresponding to the ratchet-toothed shape of the first buckle to enable the unidirectional movement of the second buckle within the second slot.

In some embodiments, the fixture includes a fixture body, the fixture body includes: a vibrating component fixing hole, the vibrating component fixing hole is coaxial with a center axis of the fixture body; and at least two inner-layer fiber fixing holes, the at least two inner-layer fiber fixing holes are distributed evenly relative to a circumference of the center axis of the fixture body, and each collecting fiber of the inner-layer fiber array is disposed on the at least two inner-layer fiber fixing holes, respectively.

In some embodiments, the vibrating component fixing hole is a wedge-shaped hole, the fixture further includes a wedge configured to insert into the wedge-shaped hole, and the wedge is configured to clamp the vibrating component into the vibrating component fixing hole.

In some embodiments, the vibrating component includes a piezoelectric ceramic tube and a single-mode fiber; the single-mode fiber is fixedly disposed on the piezoelectric ceramic tube, and protrudes and extends a fiber of a preset length at a distal end of the piezoelectric ceramic tube to form a fiber cantilever; the piezoelectric ceramic tube is configured to drive the fiber cantilever to vibrate in a resonance mode for scanning under a drive of an alternating voltage of a preset frequency; a lens set disposed on a distal end of the fiber cantilever is configured to focus dispersed light emitted by the single-mode fiber and image the sample tissue; a distance between an end of the fiber cantilever and a principal surface of an object space of the lens set matches an angle of field of view and a size of an optical spot of a circular field of view; and the piezoelectric ceramic tube and the lens set are fixedly disposed in the sleeve, the piezoelectric ceramic tube is fixedly disposed in the sleeve.

In some embodiments, an inner diameter of the inner-layer fiber collecting array and an axial position inside the sleeve are determined based on a spatial stereo angle formed by the fiber cantilever in the scanning illumination optical path during a vibrating process, thereby improving a collecting efficiency of the inner-layer fiber collecting array without interfering with the scanning illumination optical path.

In some embodiments, an inner diameter of the inner-layer fiber collecting array is greater than twice a maximum offset of the fiber cantilever and less than an inner diameter of the sleeve.

In some embodiments, a distance between an illuminated surface of the inner-layer fiber collecting array and a principal surface of an object space of the lens set is less than a distance between the distal end of the fiber cantilever and the principal surface of the object space of the lens set.

In some embodiments, an axial position of the inner-layer fiber collecting array inside the sleeve satisfies a constraint relationship:

$$\mathrm{arc}tran\frac{R}{u+L-l} > \alpha;$$

where R refers to a radius of the inner-layer fiber collecting array, u refers to a distance between a distal end of the fiber cantilever and a principal surface of an object space of the lens set, L refers to a length of the fiber cantilever, l refers to a distance between an illuminated surface of the inner-layer fiber collecting array and the principal surface of the object space of the lens set, and α refers to a deflection angle of the fiber cantilever.

In some embodiments, the axial position of an illuminated surface of the inner-layer fiber collecting array inside the sleeve is located at a focal point of the lens set.

In some embodiments, in the scanning illumination optical path, a diameter of the fiber cantilever of a single-mode fiber after a corrosion process is less than a standard diameter of the single-mode fiber.

In some embodiments, a maximum outer diameter of the scanning fiber endoscope probe is less than or equal to 1.5 mm, a length of a fiber cantilever is within a range of 2 mm to 4 mm, an imaging frame rate of the photoelectric detector is within a range of 15 fps to 25 fps, and a scanning amplitude of the fiber cantilever is within a range of 0.5 mm to 0.8 mm.

In some embodiments, the scanning fiber endoscope probe further includes an outer-fiber collecting array; the outer-layer fiber collecting array is the tubular fiber array formed by disposing a plurality of collecting fibers at a periphery of the cavity of the scanning illumination optical path and is configured to collect and transmit the portion of the detecting light scattered from or reflected by the sample issue to an exterior of the scanning illumination optical path to perform the imaging by the photoelectric detector.

In some embodiments, the inner-layer fiber collecting array includes one or two layers, and/or, the outer-layer fiber collecting array includes one or two layers.

In some embodiments, the outer-layer fiber collecting array and the inner-layer fiber collecting array form the inner-outer collecting channel, one or more fibers of the inner-outer collecting channel are evenly distributed on an inner circumference and an outer circumference of the inner-outer collecting channel, the inner-outer collecting channel is configured to collect the portion of the detecting light scattered from or reflected by the sample tissue, and a field of view of the inner-outer collecting channel is greater than a field of view of the scanning illumination optical path.

In some embodiments, the fiber of the inner-outer collecting channel is made of plastic fiber, and a numerical aperture of the collecting fiber of the inner-outer collecting channels is greater than a numerical aperture of the single-mode fiber.

According to the embodiments of the present disclosure, a scanning fiber endoscope is provided, the scanning fiber endoscope includes a scanning fiber endoscope probe and a photoelectric detector, the scanning fiber endoscope probe includes: a scanning illumination optical path and an inner-layer fiber collecting array; the scanning illumination optical path is configured to scan laser emitted by a light source to form an optical spot on a surface of a sample tissue and to form a field of view; the inner-layer fiber collecting array is configured to collect the detecting light scattered from or reflected by the sample tissue and collected through a lens set; and the photoelectric detector collects the detecting light collected by the inner-layer fiber collecting array and performs an imaging on the detecting light.

In some embodiments, the scanning fiber endoscope further includes: an outer-layer fiber collecting array, the outer-layer fiber collecting array is a tubular fiber array formed by disposing a plurality of fibers at the periphery of a cavity of the scanning illumination optical path and is configured to collect and transmit a portion of the detecting light scattered from or reflected by the sample issue to the exterior of the scanning illumination optical path to perform the imaging by the photoelectric detector.

In some embodiments, the scanning illumination optical path includes: a vibrating component, a lens set, a sleeve, and a fixture; the vibrating component is located in an proximal portion of a cavity of the sleeve and is located at a proximal end of the lens set; the inner-layer fiber collecting array is located at a proximal end of the lens set and is disposed at an outer side of the vibrating component, and the inner-layer fiber collecting array is a tubular fiber array surrounded by a plurality of fibers; the fixture fixes the vibrating component within the sleeve and fixes the inner-layer fiber collecting array between the sleeve and the vibrating component; and the inner-layer fiber collecting array is configured to collect a portion of detecting light entering a cavity of the probe through the lens set.

In some embodiments, the inner-layer fiber collecting array includes one or two layers, and/or, the outer-layer fiber collecting array includes one or two layers.

According to some embodiments of the present disclosure, a scanning fiber endoscope probe is provided, the scanning fiber endoscope probe includes: a scanning illumination optical path and an inner-layer fiber collecting array; the scanning illumination optical path is configured to perform a spiral scanning on a multi-spectral laser emitted by a plurality of light sources in a two-dimensional surface through a microelectromechanical drive device to form an optical spot on a surface of a sample tissue and to form a two-dimensional circular field of view; the inner-layer fiber collecting array is disposed within the cavity of the scanning illumination optical path and is configured to collect and transmit the detection light scattered from or reflected by the sample tissue to perform the imaging by the photoelectric detector.

In some embodiments, the scanning illumination optical path includes: a vibrating component, a lens set, a sleeve, and a fixture; the vibrating component is disposed on the proximal end of a cavity of the sleeve and is located at the proximal side of the lens set; the inner-layer fiber collecting array is located at the proximal end of the lens set and is disposed on an outer side of the vibrating component, and the inner-layer fiber collecting array is a tubular fiber array surrounded by a plurality of fibers; the fixture fixes the vibrating component within the sleeve and fixes the inner-layer fiber collecting array between the sleeve and the vibrating component, and the inner-layer fiber collecting array is configured to collect a portion of detecting light entering the cavity of the probe through the lens set.

In some embodiments, the vibrating component includes a piezoelectric ceramic tube PZT and a single-mode fiber SMF; the single-mode fiber SMF is fixedly disposed on the piezoelectric ceramic tube, and protrudes and extends a fiber of a preset length at a distal end of the piezoelectric ceramic tube to form a fiber cantilever, and the fiber cantilever vibrates freely under a drive of the piezoelectric ceramic tube PZT; the piezoelectric ceramic tube drives the fiber cantilever to vibrate in a resonance mode for scanning on a two-dimensional surface under a drive of an alternating voltage of a preset frequency; a lens set disposed on a distal end of the fiber cantilever is configured to focus dispersed light emitted by the single-mode fiber SMF and image the sample tissue; an end of the fiber cantilever has a suitable focal length to match an angle of field of view FOV and a size of an optical spot; the piezoelectric ceramic tube PZT and the lens set are fixedly disposed on a sleeve, and the piezoelectric ceramic tube PZT is disposed in the sleeve.

In some embodiments, in response to that the inner-layer fiber collecting array is a tubular fiber array surrounded by at least two collecting fibers in a uniform arrangement, a plurality of symmetrically distributed voids are preset in the inner-layer fiber collecting array, the voids are configured to mount a fixture; and an axial position and a diameter size of the inner-layer fiber collecting array inside the probe are determined according to a spatial stereo angle formed by the fiber cantilever in the scanning illumination optical path, thereby improving a collecting efficiency of the inner-layer fiber collecting array without interfering with the illumination optical path.

In some embodiments, the scanning fiber endoscope probe includes: an outer-layer fiber collecting array, and the outer-layer fiber collecting array is disposed at the periphery of the sleeve and is configured to collect and transmit the detecting light scattered from or reflected by the sample tissue to perform an imaging through a photoelectric detector.

In some embodiments, the outer-layer fiber collecting array and the inner-layer fiber collecting array form an inner-outer double-layer collecting channel, one or more fiber of the inner-outer collecting channels are made of plastic fibers POFs, one or more plastic fibers POF are evenly distributed on an inner circumference and an outer circumference of the inner-outer collecting channel, a numerical aperture of the plastic fiber POF is greater than a numerical aperture of the single-mode fiber, the inner-outer collecting channel is configured to collect the portion of the detecting light scattered from or reflected by the sample tissue, and a field of view of the inner-outer collecting channel is greater than a field of view of the scanning illumination optical path.

In some embodiments, the outer-fiber collecting array is a plurality of collecting fibers covering an outer side of the sleeve to surround a tubular fiber collecting array, and the outer-fiber collecting array is configured to collect the detecting light transmitted to the exterior of the scanning fiber endoscope probe.

In some embodiments, in the scanning illumination optical path, a diameter of the fiber cantilever of the single-mode fiber after the corrosion process is less than a preset threshold of the single-mode fiber.

According to some embodiments of the present disclosure, a scanning fiber endoscope is further provided, the endoscope includes a scanning fiber endoscope probe and a photoelectric detector, the scanning fiber endoscope probe includes: a scanning illumination optical path, an inner-layer fiber collecting array, and an outer-layer fiber collecting array; the scanning illumination optical path is configured to perform a spiral scanning on a multi-spectral laser emitted by a plurality of light sources in a two-dimensional surface through a microelectromechanical drive device to form an optical spot on a surface of a sample tissue and to form a two-dimensional circular field of view; an inner-layer fiber collecting array disposed inside a cavity of the scanning illumination optical path is configured to collect the detecting light transmitted to an outer side of the scanning fiber endoscope probe; an outer-layer fiber collecting array disposed outside the cavity of the scanning illumination optical path is configured to collect the detecting light transmitted to the exterior of the scanning fiber endoscope probe; and a photoelectric detector device is configured to collect the detecting light collected by the inner-layer collecting array and the outer-layer collecting array, and performs an imaging on the detecting light.

In some embodiments, the scanning illumination optical path includes: a vibrating component, a lens set, a sleeve, and a fixture; the vibrating component is disposed on an innermost side of the cavity of the sleeve and is located at the proximal side of the lens set; the inner-layer fiber collecting array is located at a proximal end of the lens set and is disposed on an outer side of the vibrating component, and inner-layer fiber collecting array is a tubular array surrounded by a plurality of fibers; and the fixture fixes the vibrating component inside the sleeve and fixes the inner-layer fiber collecting array between the sleeve and the vibrating component, and the inner-layer fiber collecting array is configured to collect a portion of detecting light entering a cavity of the probe through the lens set.

At least some of the foregoing embodiments may achieve the following technical effects: in some embodiments, by fully utilizing the redundant space away from the interior of the probe, the inner-layer fiber collecting array is added to the interior of the probe and is configured to collect and transmit the portion of detecting light scattered from or reflected by the sample tissue through the lens set to perform an imaging by the photoelectric detector, which may reduce an effect of speckle noise and increase the collecting efficiency of reflected light or scattered light, thereby increasing a signal-to-noise ratio and improving the imaging quality of the endoscope; in some embodiments, the outer-fiber collecting array is added to the exterior of the scanning fiber endoscope probe and is configured to collect and transmit the portion of detecting light scattered or reflected back to the exterior of the scanning illumination optical path to perform the imaging by the photoelectric detector, which may reduce the effect of speckle noise and increase the collecting efficiency of the reflected light or scattered light, thereby increasing the signal-to-noise ratio and improving the imaging quality of the endoscope.

BRIEF DESCRIPTION OF THE DRAWING

In order to illustrate the technical solutions related to the embodiments of the present disclosure, a brief introduction of the drawings referred to in the description of the embodiments is provided below. Obviously, the drawings described below are only some examples or embodiments of the present disclosure. Those skilled in the art, without further creative efforts, may apply the present disclosure to other similar scenarios according to these drawings.

Figure 1A:
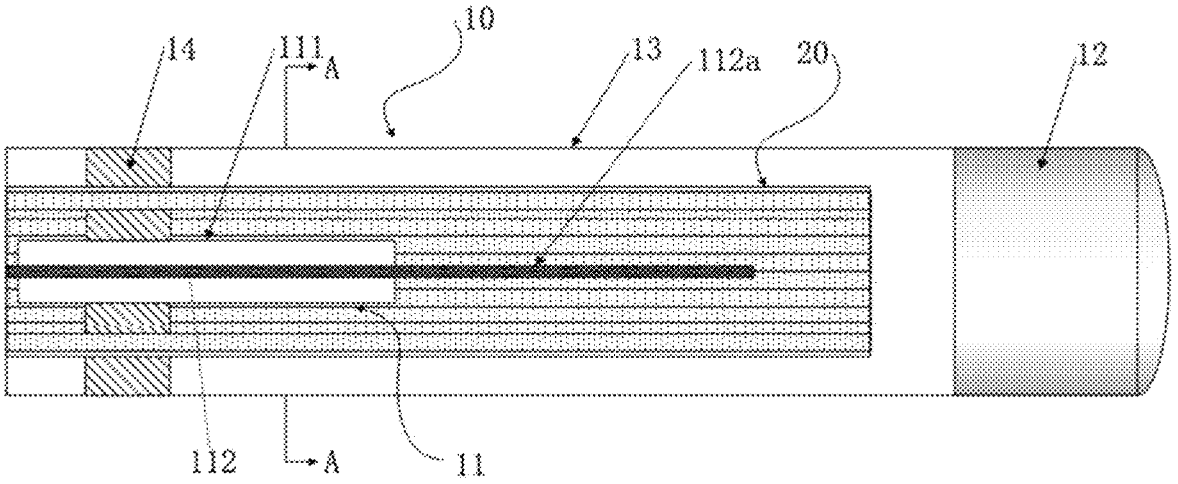
FIG. 1A is a schematic diagram illustrating a structure of a scanning fiber endoscope probe according to some embodiments of the present disclosure.

Reference numeral: scanning illumination optical path 10, vibrating component 11, lens set 12, sleeve 13, fixture 14, piezoelectric ceramic tube 111, single-mode fiber 112, fiber cantilever 112*a*, inner-layer fiber collecting array 20, outer-layer fiber collecting array 30, sample tissue 40, first fixing slot 1411, first fixing hole 1412, first slot 1413, first buckle 1414, fixture body 1421, inner-layer fiber fixing hole 1422, vibrating component fixing hole 1423, wedge 1424, second buckle 1431, second slot 1432, second fixing hole 1433, second fixing slot 1434.

DETAILED DESCRIPTION

In order to illustrate the technical solutions related to the embodiments of the present disclosure, a brief introduction of the drawings referred to in the description of the embodiments is provided below. It should be understood that the specific embodiments described herein are merely provided for the purpose of explaining the present disclosure and are not intended to limit the present disclosure. Based on the embodiments provided in the present disclosure, all other embodiments obtained by those skilled in the art without creative labor fall within the scope of protection of the present specification. Further, it should be understood that, although the efforts made in the development process may be complex and lengthy, some changes in design, manufacture, or production based on the technical contents disclosed in the present disclosure are merely conventional technical means for those skilled in the art in relation to the contents disclosed in the present disclosure, and should not be construed as an inadequate disclosure of the contents of the present disclosure.

Reference to "embodiments" in the present disclosure means that particular features, structures, or characteristics described in conjunction with the embodiments may be included in at least one embodiment of the present disclosure. The presence of the phrase at various locations in the specification does not necessarily refer to the same embodiment, nor is it a separate or alternative embodiment that is mutually exclusive of other embodiments. It is understood by those skilled in the art, both explicitly and implicitly, that the embodiments described in the present disclosure may be combined with other embodiments without conflict.

Unless otherwise defined, technical terms or scientific terms referred to in the present disclosure shall have the ordinary meaning understood by a person of ordinary skill in the technical field to which the present disclosure pertains. The words "one," "a," "a kind of," "some" and the like in the present disclosure do not indicate a limitation of quantity. They may be used in the singular or plural. The terms "including," "comprising," "having" and any variations thereof, as used in the present disclosure, are intended to cover non-exclusive compositions; e.g., processes, methods, or methods that include a series of steps or modules (units). For example, a process, method, system, product or apparatus that includes a series of steps or modules (units) is not limited to the listed steps or units, but may also include steps or units that are not listed, or may also include other steps or units that are inherent to the process, method, product or apparatus. The present disclosure does not limit the use of the words "connection," "connected," "coupled" and the like to physical or mechanical connections, but may include electrical connections, whether direct or indirect. They may include electrical connections, whether direct or indirect. As used in the present disclosure, "more than one" means more than or equal to two. The term "and/or" describes an association relationship of the associated objects and indicates that three types of relationships may exist, for example, "A and/or B" may indicate the existence of A alone, the existence of both A and B, and the existence of B alone. The terms "first," "second," "third", etc., as used in the present disclosure, are used only to distinguish similar objects and do not represent a specific ordering of the objects.

In some embodiments, a scanning fiber endoscope probe is provided, the scanning fiber endoscope probe may include a scanning illumination optical path and an inner-layer fiber collecting array.

In some embodiments, the scanning illumination optical path includes a lens set, and the scanning illumination optical path is configured to pass the emitted laser through for scanning to form an optical spot on a surface of a sample tissue and to form a field of view (e.g., a two-dimensional circular field of view). In some embodiments, the scanning illumination optical path may use multi-spectral lasers emitted by a plurality of light sources to perform a scanning. In some embodiments, the scanning illumination optical path may utilize a mono-spectral laser emitted by a single light source to perform the scanning. In some embodiments, the scanning illumination optical path may perform a spiral scanning on a two-dimensional plane. In some embodiments, the scanning illumination optical path may perform other shapes of scanning, such as a variable-diameter circular ring scanning, in which one circle is scanned and then the radius is adjusted to scan the next circle.

In some embodiments, the scanning illumination optical path may include a microelectromechanical drive device, a single-mode fiber, a lens set, a sleeve, and the like. The microelectromechanical drive device, the single-mode fiber, and the lens set are disposed in a cavity of the sleeve. The microelectromechanical drive device is configured to drive the single-mode fiber to perform the scanning. In some embodiments, the microelectromechanical drive device may be a motor actuator, an electrothermal actuator, an electromagnetic actuator, a piezoelectric actuator, or other forms of actuators. The piezoelectric actuator may be a piezoelectric ceramic tube.

In some embodiments, an inner-layer fiber collecting array is configured to collect and transmit a portion of detecting light scattered from or reflected by the sample tissue through the lens set to perform the imaging by a photoelectric detector. In some embodiments, a cavity of the illumination optical path may be a cavity of the sleeve. In some embodiments, after the light emitted by the scanning illumination optical path is focused on the sample tissue, the detecting light signal reflected by or scattered from the sample tissue may be divided into two portions. A portion of the detecting light is transmitted to a periphery of the probe, and another portion of the detecting light enters into the cavity of the probe through the lens. The portion of the detecting light entering into the probe cavity may be divided into a confocal beam and a non-confocal beam, the confocal beam refers to a beam of the detecting light reflected by or scattered from the sample tissue that is incident into a receiving range of a numerical aperture of the single-mode fiber after being converged by the lens; otherwise, the confocal beam is non-confocal. The non-confocal detecting light incident to the probe interior through the lens set is collected by the inner-layer fiber collecting array.

Some of the foregoing embodiments may increase a collecting efficiency of the detection light by providing an inner-layer fiber collecting array inside the cavity of the scanning illumination optical path, thereby solving a problem of inefficient collection of a light energy signal and improving the imaging quality of the scanning fiber endoscope. Since some of the foregoing embodiments increase the collecting efficiency of the detecting light, such that in response to that the image quality is ensured to not decrease, a volume of the scanning fiber endoscope probe may be further reduced by reducing a radial size of the cavity of the scanning illumination optical path.

Figure 1B:
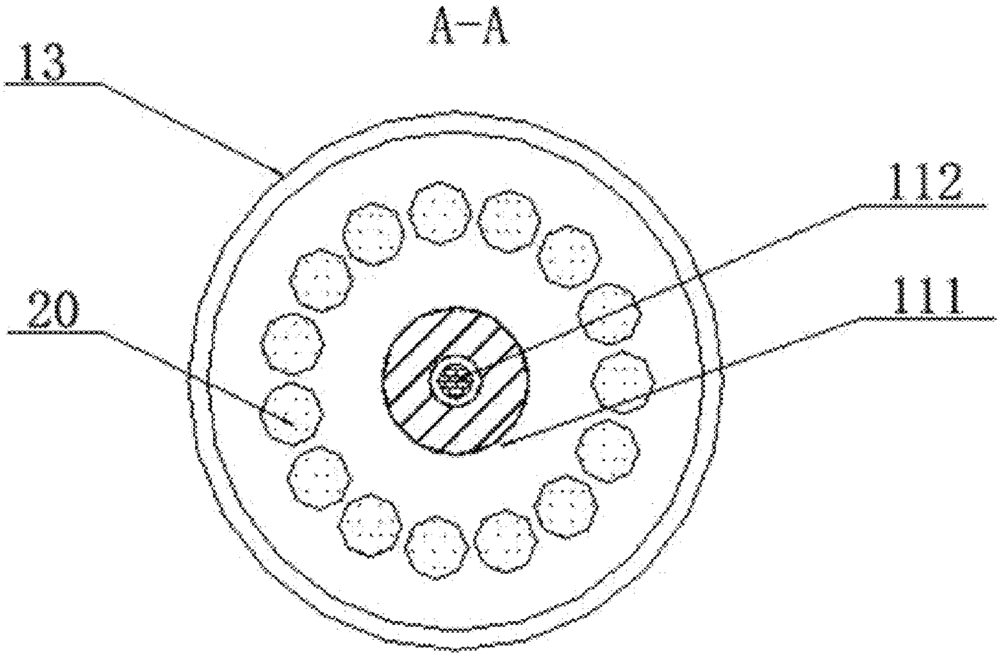
FIG. 1B is a schematic diagram illustrating a sectional view of a scanning fiber endoscope probe of FIG. 1 along AA according to some embodiments of the present disclosure.

FIG. 1A is a schematic diagram illustrating a structure of a scanning fiber endoscope probe according to some embodiments of the present disclosure. FIG. 1B is a schematic diagram illustrating a sectional view of a scanning fiber endoscope probe of FIG. 1 along AA according to some embodiments of the present disclosure.

As shown in FIG. 1A and FIG. 1B, in some embodiments, the scanning fiber endoscope probe may include a scanning illumination optical path 10 and an inner-layer fiber collecting array 20. In some embodiments, the scanning illumination optical path 10 may include a lens set 12 and a sleeve 13, and the inner-layer fiber collecting array 20 is fixed in a cavity of the sleeve 13. The inner-layer fiber collecting array is configured to collect a portion of detecting light scattered from or reflected by the sample tissue and guide the portion of detecting light to enter into the sleeve 13 through the lens set 12. In some embodiments, the inner-layer fiber collecting array may be a tubular fiber array surrounded by at least two fibers in a uniform arrangement. The uniform arrangement refers that each collecting fiber of the inner-layer fiber collecting array is provided in equal intervals around a circumference of the fiber array. In some embodiments, the inner-layer fiber collecting array may be a tubular fiber array surrounded by the plurality of collecting fibers in a non-uniform arrangement. The non-uniform arrangement refers that intervals of each collecting fiber of the inner-layer fiber collecting array around the circumference of the fiber array are partially different or entirely different.

In some embodiments, the scanning illumination optical path 10 may include a vibrating component 11, a lens set 12, a sleeve 13, and a fixture 14. In some embodiments, the vibrating component 11 may include a piezoelectric ceramic tube 111 (PTZ), and a single-mode fiber 112 (SMF). In some embodiments, the vibrating component 11 may be disposed within the cavity of the sleeve 13 and located at a proximal end of the lens set 12, and the inner-layer fiber collecting array 20 is disposed at a proximal end of the lens set 12 and is disposed on an outer side of the vibrating component 11. The proximal end refers to an end close to the user. In some embodiments, the fixture 14 fixes the inner-layer fiber collecting array 20 between the sleeve 13 and the vibrating component 11.

In some embodiments, there may be two fixtures 14, one fixture 14 is configured to fix the inner-layer fiber collecting array 20, and another fixture 14 is configured to fix the vibrating component 11.

In some embodiments, the inner-layer fiber collecting array 20 may be disposed at the proximal end of the lens set 12 and disposed on an outer side of the vibrating component 11, and the inner-layer fiber collecting array 20 may be mounted inside the fixture 14. More descriptions of the structure of the fixture 14 may be found in FIG. 3A, FIG. 3B, and FIG. 4 and the following descriptions thereof.

In some embodiments, the inner-layer fiber collecting array 20 may be disposed at the proximal end of the lens set 12 and disposed on the outer side of the vibrating component 11, and the inner-layer fiber collecting array 20 may be disposed on an outer side of the fixture 14. More descriptions of the structure of the fixture 14 may be found in FIG. 2A, FIG. 2B, FIG. 5A, FIG. 5B and the following descriptions thereof. In some embodiments, the inner-layer fiber collecting array 20 may be provided on the outer side of the fixture 14 by bonding.

In some embodiments, a single-mode fiber 112 may be fixedly disposed on the piezoelectric ceramic tube 112 and protrudes and extends a fiber cantilever 112*a* of a preset length at a distal end of the piezoelectric ceramic tube, and the fiber cantilever 112*a* is free to vibrate under a drive of the piezoelectric ceramic tube 112. The distal end refers to an end where the endoscopy probe is inserted into a body cavity of a patient. In some embodiments, under a drive of an alternating voltage (e.g., ±50 v) of a preset frequency, a piezoelectric ceramic tube 112 drives the fiber cantilever 112*a* to perform the scanning in a two-dimensional surface in a resonance mode, and a control signal of the piezoelectric ceramic tube 112 has sufficient drive frequency to satisfy an imaging frame rate and the imaging quality of the photoelectric detector.

In some embodiments, a drive frequency of the control signal of the piezoelectric ceramic tube 112 may be within a range of 5 to 10 KHz. In some embodiments, the drive frequency of the control signal of the piezoelectric ceramic tube 112 may be 9.75 kHz. In some embodiments, the drive frequency of the control signal of the piezoelectric ceramic tube 112 may be 5.46 kHz. In some embodiments, the drive frequency of the control signal of the piezoelectric ceramic tube 112 may be within a range of 7 to 8 kHz. In some embodiments, the drive frequency of the control signal of the piezoelectric ceramic tube 112 may be 7.5 kHz.

In some embodiments, an image pixel of the photoelectric detector is greater than 500*500. In some embodiments, the minimum optical resolution of the image of the photoelectric detector may be 71 p/mm. In some embodiments, an imaging frame rate of the photoelectric detector may be within a range of 15 fps to 25 fps.

In some embodiments, the end of the fiber cantilever 112*a* has a sufficient vibration amplitude to satisfy an imaging range of the endoscopic probe. In some embodiments, the vibration amplitude of the fiber cantilever 112*a* may be within a range of 0.5 to 0.8 mm. In some embodiments, the length of the fiber cantilever 112*a* may be within a range of 2 to 4 mm. In some embodiments, the lens set 12 may be disposed at a distal end of the fiber cantilever 112*a* to focus dispersed light emitted by the single-mode fiber 112 and image on the sample tissue. In some embodiments, a distance between the end of the fiber cantilever 112*a* and a principal surface of an object space of the lens set 12 matches a field of view angle of a circular field of view and a size of the optical spot. In some embodiments, a diameter of the circular field of view may be within a range of 2 to 12 mm. In some embodiments, the diameter of the circular field of view may be 2.2 mm. In some embodiments, a diameter of the circular field of view may be 10 mm. In some embodiments, the piezoelectric ceramic tube 112 and the lens set 12 may be fixedly disposed on the sleeve 13, and the piezoelectric ceramic tube 112 may be disposed inside the sleeve 13 by the fixture 14. In some embodiments, the vibration amplitude of the fiber cantilever 112*a* may be adjusted according to different needs of imaging. In some embodiments, the vibration amplitude of the fiber cantilever 112*a* may be within a range of 0.1 to 0.5 mm. For example, the vibration amplitude of the fiber cantilever 112*a* may be 0.1 mm, 0.11 mm, 0.3 mm, 0.5 mm, and the like.

In a specific embodiment, a length of the fiber cantilever may be within a range of 2 to 3 mm, the drive frequency of the control signal of the piezoelectric ceramic tube 112 may be 5.46 kHz, the imaging frame rate of the photoelectric detector may be 15 fps, the diameter of the circular field of view at this time may be 10 mm, and the vibration amplitude of the fiber cantilever 112*a* may be 0.5 mm. In a specific embodiment, the length of the fiber cantilever may be within a range of 2 to 3 mm, the drive frequency of the control signal of the piezoelectric ceramic tube 112 may be 9.75 kHz, the imaging frame rate of the photoelectric detector may be 25 fps, the diameter of the circular field of view at this time may be 2.2 mm, and the vibration amplitude of the fiber cantilever 112*a* may be 0.11 mm.

In some embodiments, when the fiber arrangement on the inner-layer fiber collecting array 20 is a tubular uniform distributed structure, a plurality of symmetrically distributed voids may be preset in the inner-layer fiber collecting array 20, and the voids are configured to mount the fixture 14. More descriptions of the specific structure of the fixture may be found in FIG. 2A-FIG. 5B and their related descriptions, which will not be repeated herein.

In some embodiments, an inner diameter of the inner-fiber collecting array 20 and an axial position inside the endoscope probe may be determined based on a spatial stereo angle formed by the fiber cantilever 112*a* in the scanning illumination optical path 10, thereby improving the collecting efficiency of the inner-layer fiber collecting array 20 for collecting the detecting light without interfering with the scanning illumination optical path.

Figure 8:
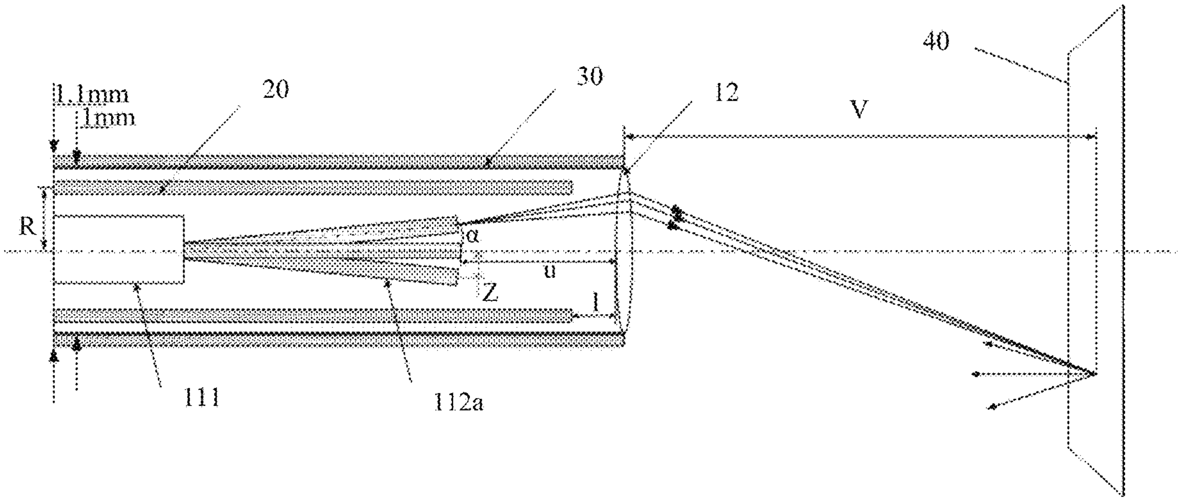
FIG. 8 is a schematic diagram illustrating an overall principle of a scanning fiber endoscope system according to some embodiments of the present disclosure.

In some embodiments, the spatial stereo angle formed by the fiber cantilever 112*a* may be twice a deflection angle α of the fiber cantilever 112*a* shown in FIG. 8.

In some embodiments, a distance between an illuminated surface of the inner-layer fiber collecting array 20 and the principal surface of the object space of the lens set 12 is less than a distance between the distal end of the fiber cantilever and the principal surface of the object space of the lens set to allow a vibration of the fiber cantilever to not interfere with a collection of the detecting light by the inner-layer fiber collecting array 20 and may increase the amount of detecting light received by the inner-layer fiber collecting array 20.

In some embodiments, a distance between the illuminated surface of the inner-layer fiber collecting array 20 and the principal surface of the object of the lens set 12 may be greater than or equal to a distance between the distal end of the fiber cantilever and the principal surface of the object of the lens set 12, in this circumstances, the vibration of the fiber cantilever 112*a* does not interfere with the collection of detecting light by the inner-layer fiber collecting array 20. For example, the axial position of the illuminated surface of the inner-layer fiber collecting array 20 inside the sleeve may be disposed behind the spatial stereo angle formed by the scanning illumination optical path 10. In some embodiments, by setting the distance between the illuminated surface of the inner-layer fiber collecting array 20 and the principal surface of the object of the lens set 12 to be greater than or equal to the distance between a distal end of the fiber cantilever and the principal surface of the object of the lens set 12, a space in an inner cavity of the scanning fiber endoscope probe may be effectively used, and an external size of the lens set may be reduced on the basis of ensuring the circular field of view range.

Figure 2A:
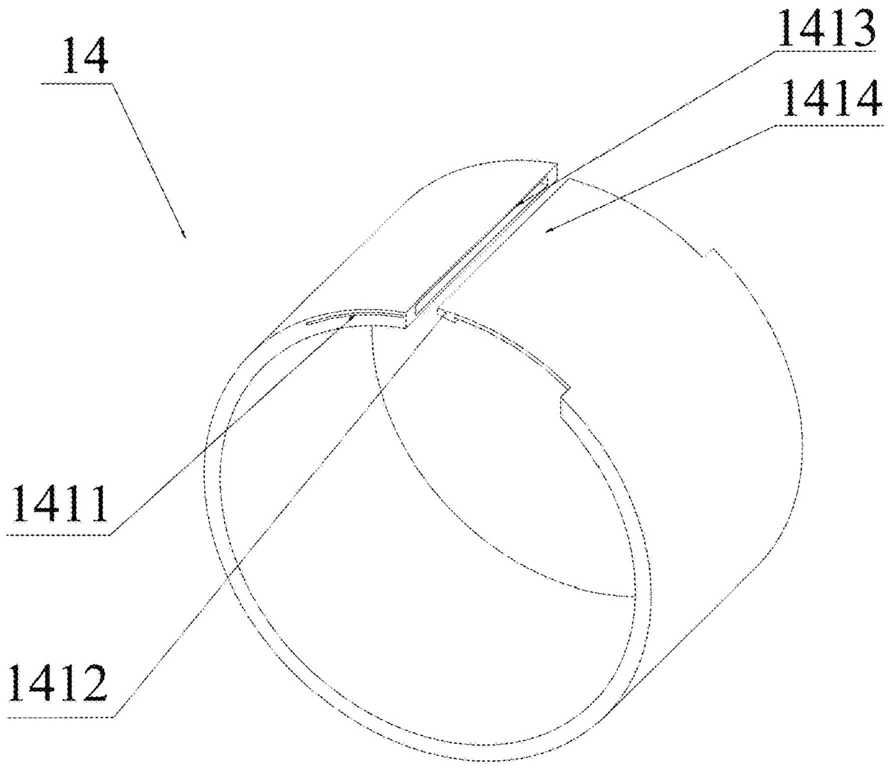
FIG. 2A is a schematic diagram illustrating a structure of a fixture according to some embodiments of the present disclosure.
Figure 2B:
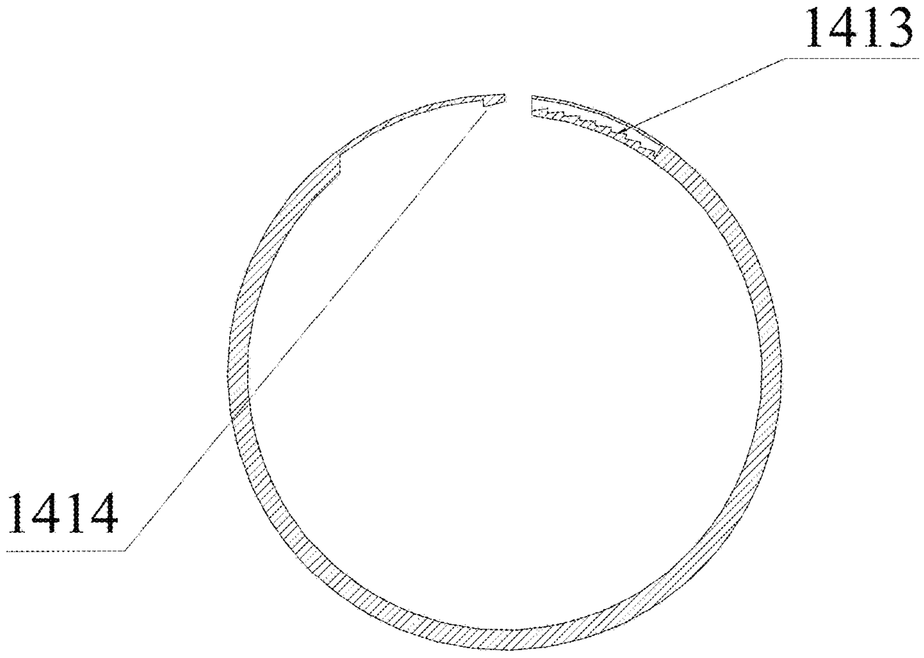
FIG. 2B is a schematic diagram illustrating a sectional view of a fixture of FIG. 2A.

FIG. 2A is a schematic diagram illustrating a structure of a fixture according to some embodiments of the present disclosure. FIG. 2B is a schematic diagram illustrating a sectional view of a fixture of FIG. 2A.

As shown in FIG. 2A and FIG. 2B, in some embodiments, the fixture 14 may be a circular ring with an opening, one end of the opening of the circular ring is provided with a first buckle 1414, another end of the opening of the circular ring is provided with a first slot 1413. The first buckle is inserted into the first slot 1413, and then the first buckle 1414 and the first slot 1413 are fixed relative to each other by using a first fixing member.

In some embodiments, a side of the first buckle 1414 is provided with a first fixing hole 1412, a side of the first slot 1413 is provided with a first fixing slot 1411, and after the first buckle 1414 is inserted into the first slot 1413, a position of the first fixing hole 1412 corresponds to a position of the first fixing slot 1411, the first buckle 1414 is passed through the first fixing slot 1411 and then inserted into the first fixing hole 1412, and then the first buckle 1414 and the first slot 1413 are relatively fixed. In some embodiments, the first fixing member may be a screw and the first fixing hole 1412 may be a screw hole.

In some embodiments, the first slot 1413 may be bar-shaped, and after the first fixing member is passed through the first fixing slot 1411 and then inserted into the first fixing hole 1412, the first buckle 1414 and the first slot 1413 may have a relative displacement not exceeding the length of the first fixing slot 1411.

In some embodiments, the first buckle 1414 may be in a ratchet-toothed shape, and the first slot 1413 is provided with a protrusion matching the ratchet-toothed shape of the first buckle 1414 to enable unidirectional movement of the first buckle 1414 within the first slot 1413, thereby realizing a tightening of each fiber of the inner-layer fiber collecting array 20. Through a corresponding arrangement of the ratchet-toothed shape and the projection, the fixture 14 may be mounted conveniently, and a clamping effect on the optical fiber may be good.

Figure 3A:
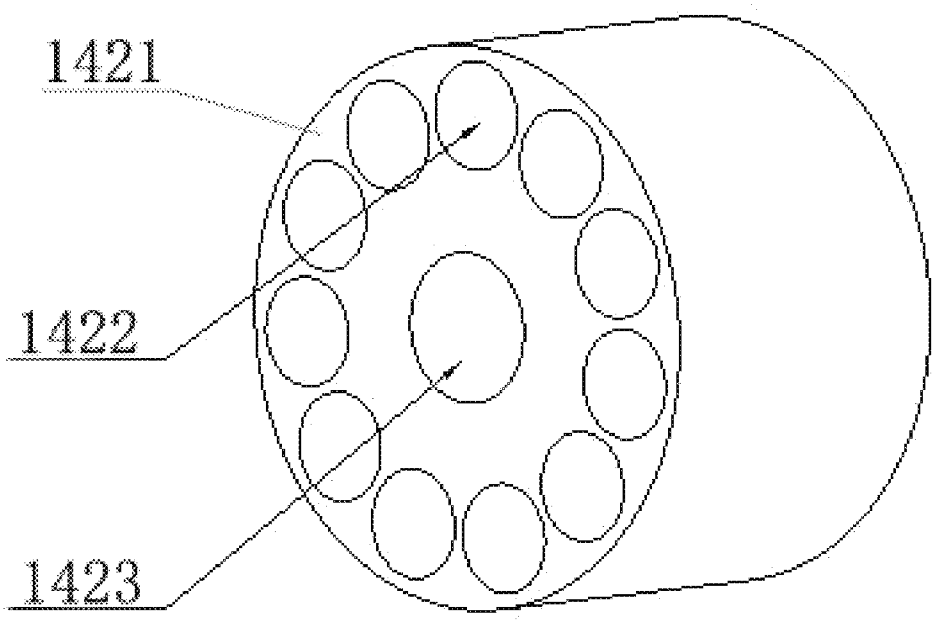
FIG. 3A is a schematic diagram illustrating a structure of a fixture according to some embodiments of the present disclosure.
Figure 3B:
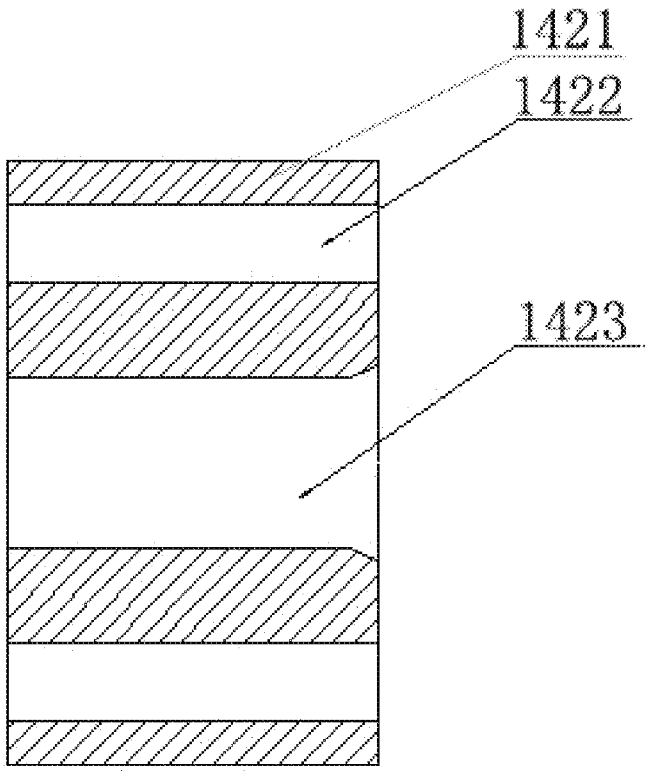
FIG. 3B is a schematic diagram illustrating a sectional view of a fixture of FIG. 3A.

FIG. 3A is a schematic diagram illustrating a structure of a fixture according to some embodiments of the present disclosure. FIG. 3B is a schematic diagram illustrating a sectional view of a fixture of FIG. 3.

As shown in FIGS. 3A and 3B, in some embodiments, the fixture body 14 may include a fixture body 1421. The fixture body 1421 may be provided with a vibrating component fixing hole 1423 and at least two inner-layer fiber fixing holes 1422. The vibrating component fixing hole 1423 is configured to mount the vibrating component 11, and the at least two inner-layer fiber fixing holes 1422 are configured to mount each collecting fiber of the inner-layer fiber collecting array 20. In some embodiments, the vibrating component 1423 may be coaxial with a center axis of the fixture body 1421. In some embodiments, the at least two inner-layer fiber fixing holes 1422 may be distributed evenly relative to a circumference of the center axis of the fixture body, and each collecting fiber of the inner-layer fiber array 20 is disposed on the at least two inner-layer fiber fixing holes 1422, respectively.

In some embodiments, a diameter of the vibrating component fixing hole 1423 may be slightly smaller than a diameter of the vibrating component 11 to provide an interference fit between the vibrating component 11 and the vibrating component fixing hole 1423.

In some embodiments, as shown in FIG. 3B, an opening end of the vibrating component fixing hole 1423 may be provided with a bevel with a slope to facilitate assembly of the vibrating component 11.

In some embodiments, the diameter of the vibrating component fixing hole 1423 may be equal to or slightly greater than the diameter of the vibrating component 11, and the vibrating component 11 is fixed in the vibrating component fixing hole 1423 by evenly coating the vibrating component fixing hole 1423 with an adhesive substance (e.g., glue).

Figure 4:
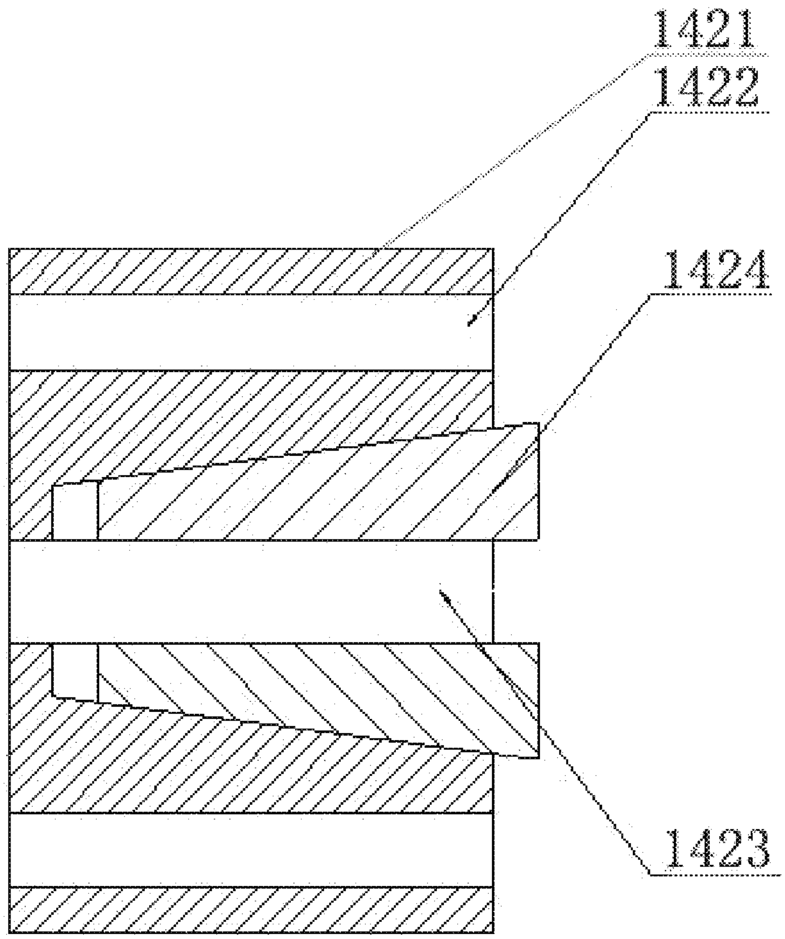
FIG. 4 is a schematic diagram illustrating a structure of a fixture according to some embodiments of the present disclosure.

In some embodiments, the vibrating component fixing hole 1423 may be a wedge-shaped hole, and the fixture 14 may further include a wedge 1424 configured to be inserted into the wedge-shaped hole, and the wedge 1424 is configured to clamp the vibrating component 11 into the vibrating component fixing hole 1423 as shown in FIG. 4.

Figure 5A:
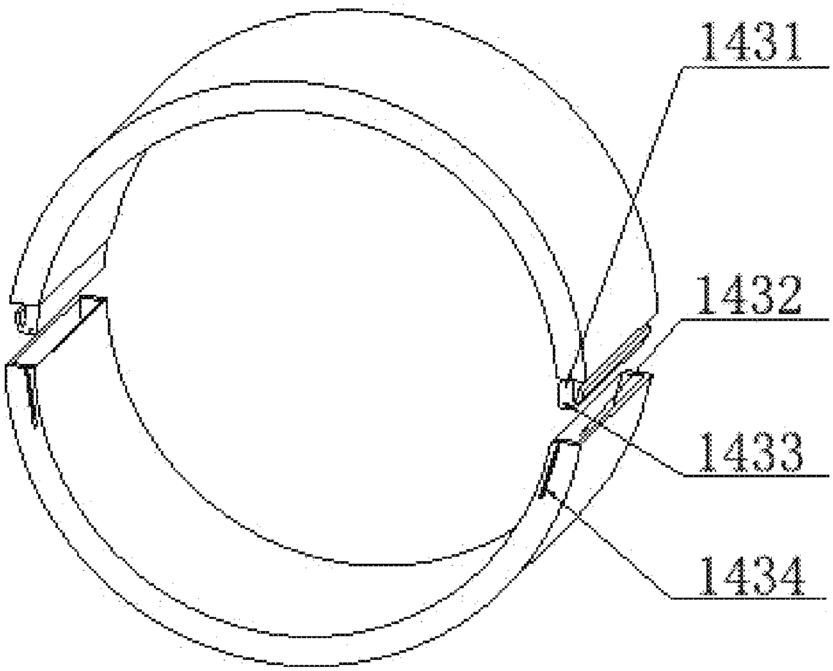
FIG. 5A is a schematic diagram illustrating a structure of a fixture according to some embodiments of the present disclosure.
Figure 5B:
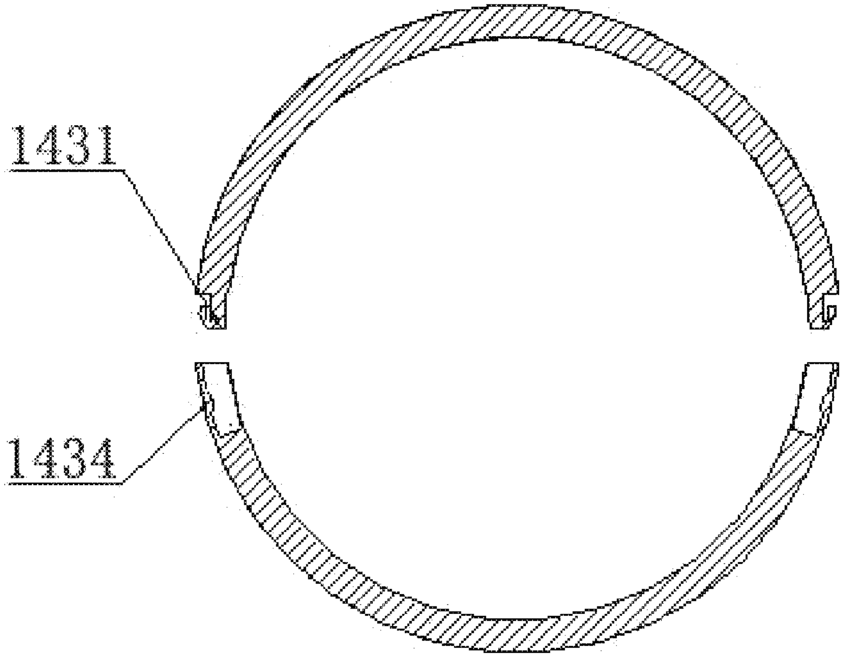
FIG. 5B is a schematic diagram illustrating a sectional view of a fixture of FIG. 5A.

FIG. 5A is a schematic diagram illustrating a structure of a fixture according to some embodiments of the present disclosure. FIG. 5B is a schematic diagram illustrating a sectional view of a fixture of FIG. 5A.

As shown in FIG. 5A and FIG. 5B, in some embodiments, the fixture 14 may be divided into a first half-circular ring and a second half-circular ring, each of two ends on the first half-circular ring is respectively provided with a second buckle 1431. Each of two ends on the second half-circular ring is provided with a second slot 1432, the first buckle 1414 is inserted into the second slot 1432, and then the first buckle 1414 and the second slot 1432 are fixed relative to each other by using a second fixing member.

In some embodiments, a side of the second buckle 1431 is provided with a second fixing hole 1433, a side of the second slot 1432 is provided with a second fixing slot 1434, and after the second buckle 1431 is inserted into the second slot 1432, a position of the second fixing hole 1433 corresponds to a position of the second fixing slot 1434, the second buckle 1431 is passed through the second fixing slot 1434 and then inserted into the second fixing hole 1433. Then the second buckle 1431 and the second slot 1432 are relatively fixed. In some embodiments, the second fixing member may be a screw and the second fixing hole 1433 may be a screw hole In some embodiments, the second slot 1432 may be a bar-shaped slot, and after the second fixing member is passed through the second fixing slot 1434 and then inserted into the second fixing hole 1433, the second buckle 1431 and the second slot 1432 may have a relative displacement not exceeding the length of the second fixing slot 1434.

In some embodiments, the second buckle 1431 may be ratchet-toothed shaped, and the second slot 1432 is provided with a protrusion corresponding to the ratchet-toothed shape of the second buckle 1431 to enable a unidirectional movement of the second buckle 1431 within the second slot 1432, thereby realizing the tightening of each fiber of the inner-layer fiber collecting array 20.

Figure 6A:
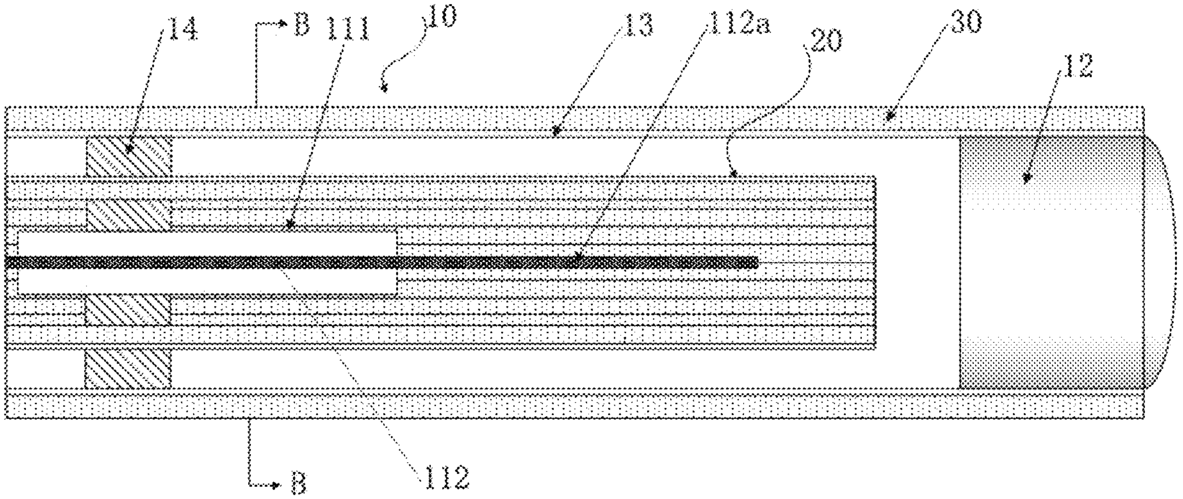
FIG. 6A is another schematic diagram illustrating a structure of a scanning fiber endoscope probe according to some embodiments of the present disclosure.
Figure 6B:
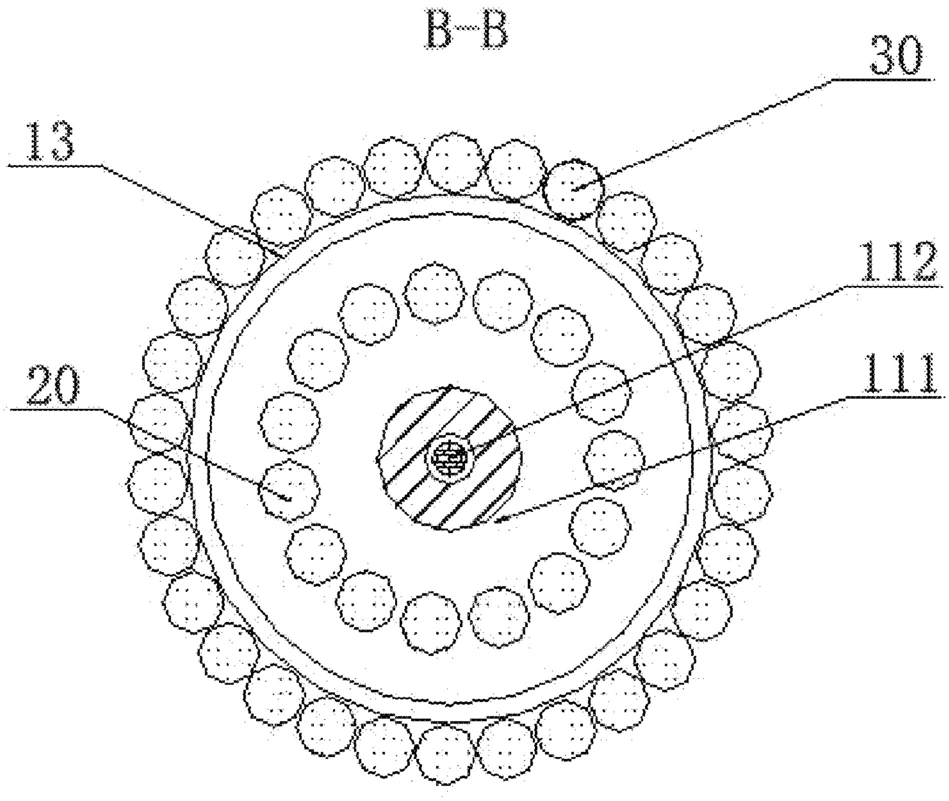
FIG. 6B is a schematic diagram illustrating a sectional view of a scanning fiber endoscope probe in FIG. 6A along BB according to some embodiments of the present disclosure.

FIG. 6A is a schematic diagram II illustrating a structure of a scanning fiber endoscope probe according to some embodiments of the present disclosure. FIG. 6B is a schematic diagram illustrating a sectional view of a scanning fiber endoscope probe in FIG. 6A along BB according to some embodiments of the present disclosure.

As shown in FIG. 6A and FIG. 6B, in some embodiments, the scanning fiber endoscope probe may include a scanning illumination optical path 10, an inner-fiber collecting array 20, and an outer-fiber collecting array 30.

In some embodiments, the scanning illumination optical path 10 is configured to scan the laser emitted by a light source to form an optical spot on the surface of a sample tissue and to form a two-dimensional circular field of view. In some embodiments, the scanning illumination optical path 10 may drive a single-mode fiber to scan through a microelectromechanical drive. In some embodiments, the microelectromechanical drive device may be a motor actuator, an electrothermal actuator, an electromagnetic actuator, a piezoelectric actuator, or other forms of actuators. The piezoelectric actuator may be a piezoelectric ceramic tube.

In some embodiments, an inner-layer fiber collecting array 20 is disposed within the cavity of the scanning illumination optical path 10 and is configured to collect and transmit the detection light scattered from or reflected by the sample tissue to perform the imaging by the photoelectric detector.

The outer-layer fiber collecting array 30 is a tubular fiber array formed by disposing a plurality of collecting fibers at the periphery of a cavity of the scanning illumination optical path and is configured to collect and transmit a portion of the detecting light scattered from or reflected by the sample issue back to the exterior of the scanning illumination optical path to perform imaging by the photoelectric detector. In some embodiments, the outer-fiber collecting array 30 may include a plurality of collecting fibers disposed on the periphery of the cavity of the sleeve 13.

The outer-layer fiber collecting array 30 and the inner-layer fiber collecting array 20 may form an inner-outer collecting channel. In some embodiments, the collecting fiber of the inner-outer collecting channel may be made of plastic fiber. In some embodiments, one or more collecting fibers of the inner-outer collecting channel are evenly distributed on the inner circumference and the outer circumference of the inner-outer collecting channel, the inner-outer collecting channel is configured to collect a portion of detecting light scattered from or reflected by the sample tissue, and a field of view of the inner-outer collecting channel is greater than a field of view of the scanning illumination optical path. In some embodiments, a numerical aperture of the collecting fiber of the inner-outer collecting channel may be greater than a numerical aperture of the single-mode fiber 112.

In some embodiments, the maximum outer diameter of the scanning fiber endoscope probe is less than or equal to 1.5 mm.

In some embodiments, the inner-layer fiber collecting array 20 may include one or two layers, and/or, the outer-layer fiber collecting array 30 may include one or two layers. For example, the inner-layer fiber collecting array 20 includes one layer and the outer-layer fiber collecting array 30 includes two layers. As another example, the inner-layer fiber collecting array 20 includes two layers and the outer-layer fiber collecting array 30 includes one layer. As another example, the inner-layer fiber collecting array 20 includes two layers and the outer-layer fiber collecting array 30 includes two layers. By setting the inner-layer fiber collecting array 20 and/or the outer-layer fiber collecting array 30 to include two layers, the collecting efficiency of the detecting light may be further improved.

Figure 7:
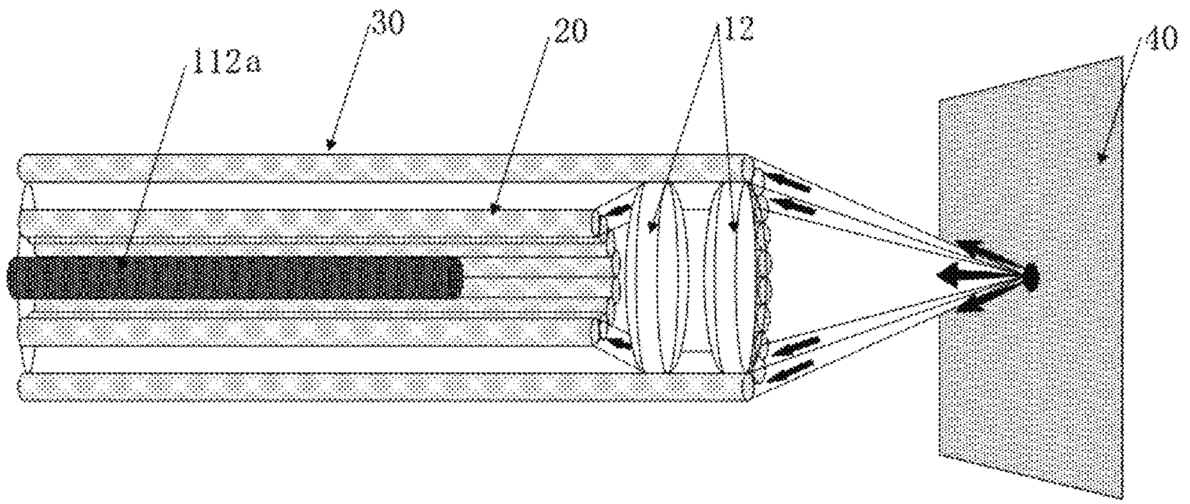
FIG. 7 is a schematic diagram illustrating an operation of an inner-outer collecting channel according to some embodiments of the present disclosure.

FIG. 7 is a schematic diagram illustrating an operation of an inner-outer collecting channel according to some embodiments of the present disclosure.

As shown in FIG. 7, in some embodiments, the detecting light reflected or scattered by the sample tissue 40 includes two portions, one portion of detecting light transmitted to the periphery of the endoscopic probe is collected by the outer-layer fiber collecting array 30, and the other portion of detecting light entering the inner cavity of the endoscopic probe through the lens set 12 is collected by the inner-layer fiber collecting array 20.

In some of the foregoing embodiments, by fully utilizing the redundant space away from the interior of the probe, the inner-layer fiber collecting array is added to the interior of the probe and is configured to collect and transmit the portion of detecting light scattered from or reflected by the sample tissue through the lens set to perform the imaging by the photoelectric detector, which may reduce an effect of speckle noise and increase the collecting efficiency of reflected light or scattered light, thereby increasing a signal-to-noise ratio and improving the imaging quality of the endoscope.

In some embodiments, the diameter of the fiber cantilever of the single-mode fiber in the scanning illumination optical path after a corrosion process is less than a standard diameter of the single-mode fiber. The diameter fiber cantilever with a smaller diameter may reach a greater resonant frequency and a greater lateral offset, achieving an overall grater scanning rate and a greater imaging range of the scanning fiber endoscope probe. In some embodiments, the diameter of the fiber cantilever 112*a* in the scanning illumination optical path is less than the diameter of the single-mode fiber 112 at other locations. By reducing the diameter only at the fiber cantilever 112*a*, the processing efficiency may be improved and the processing cost may be saved, and the single-mode fiber 112 may also be made to fit securely with the piezoelectric ceramic tube 111.

FIG. 8 is a schematic diagram illustrating an overall principle of a scanning fiber endoscope system according to some embodiments of the present disclosure.

As shown in FIG. 8, to expand analysis of the scanning illumination optical path 10, the single-mode fiber 112 is fixed in the piezoelectric ceramic tube 111 with a free section of the fiber cantilever 112*a*, and the fiber cantilever is driven to vibrate in a resonance mode by applying an alternating voltage signal of a certain frequency to the piezoelectric ceramic tube 111.

As shown in equation 1, a resonant frequency is determined by the mechanical properties of the fiber cantilever:

$$F = \frac{\pi\sqrt{E}}{16\sqrt{\rho}} r/L^2, \quad (1);$$

where F is a resonant frequency of the fiber cantilever, E is an elastic modulus of the fiber cantilever, ρ is a density of the fiber cantilever, r is a radius of the fiber cantilever, and L is a length of the fiber cantilever.

As shown in equation 2, an amplitude of the fiber cantilever is determined by the mechanical properties of the piezoelectric ceramic tube and the mechanical properties of the fiber cantilever:

$$z = \frac{WL^3}{3EI}, \quad (2);$$

where z is the amplitude of the fiber cantilever, W is stress applied to the fiber cantilever by the piezoelectric ceramic tube, I is a moment of inertia of the fiber cantilever, and L is the length of the fiber cantilever.

A vibrating fiber cantilever forms a certain deflection angle with a direction of an optical axis of the endoscope probe, as shown in equation 3. The deflection angle is jointly determined by the length of the fiber cantilever and the amplitude of the fiber cantilever:

$$\alpha = \arctan\frac{Z}{L}, \quad (3);$$

where a is the deflection angle of the fiber cantilever and L is the length of the fiber cantilever.

The end of the fiber cantilever emits a laser beam with a certain divergence angle, and the beam enters the lens set 12 after a certain distance of transmission, and the beam is focused on the sample tissue 40 after passing through the lens set 12, which exists in an imaging relationship as in equation 4:

$$\frac{1}{f} = \frac{1}{u} + \frac{1}{v}, \quad (4);$$

where f is a focal length of the lens set 12, u is a distance between the distal end of the fiber cantilever and the principal surface of the object space of the lens set 12 (i.e., an object distance), and v is the distance between an emission surface of the lens set 12 and the sample tissue 40 (i.e., an image distance).

The vibrating amplitude of the fiber cantilever and an image-object relationship of the lens set 12 jointly determine an imaging range of the scanning illumination optical path and an angle of field of view of the scanning illumination optical path.

The inner-outer collecting channel of the endoscope probe is further analyzed, as shown in FIG. 8, the detecting light reflected by or scattered from the sample tissue 40 may be divided into two portions, one portion of the detecting light is irradiated on a receiving surface of the outer-fiber collecting array 30 at the periphery of the endoscope probe, and the other portion of detecting light is incident on the receiving surface of the inner-fiber collecting array 20 inside an inner cavity of the endoscope probe through the lens set 12. The detecting light irradiated on the receiving surface of the inner and outer collecting fiber arrays is collected and transmitted to the photoelectric detector, and the luminous flux of the detecting light is jointly determined by an optical intensity of the detecting light that is scattered or reflected, a numerical aperture of the collecting fibers, an angle of incidence of the light, and an area of the receiving surface of the collecting fibers. The illuminance of the receiving surface has an expression as shown in equation 5:

$$E = \frac{d\phi}{dA} = \frac{LdA_s\cos\theta_1\cos\theta_2}{r^2}, \quad (5);$$

where E is the illuminated surface of the receiving surface of the collecting fiber, Ø is the luminous flux of the receiving surface of the collecting fiber, $A_S$ is a luminous surface element of the fiber cantilever, dA is an illuminated surface element of the collecting fiber, and $\theta_1$ and $\theta_2$ are the angles between the normals of a luminous surface of the fiber cantilever and a receiving surface of the collecting fiber and a distance r, respectively.

The luminous flux at the receiving surface of the collecting fiber is an integral of the illuminance to which the receiving surface of the collecting fiber is subjected, as shown in equation 6:

$$\phi = \int E dA, \quad (6);$$

Not all of the light beam illuminating the receiving surface of the collecting fiber is efficiently collected, and merely the light smaller than the range of numerical apertures of the collecting fiber is received and transmitted to the photoelectric detector, which depends on the size of the numerical aperture of the collecting fiber as shown in equation 7:

$$NA = n\sin\frac{\beta}{2}, \quad (7);$$

where NA is the numerical aperture of the collecting fiber, n is a refractive index of the emission medium, and β is a receiving angle of the beam. The detecting light is collected and transmitted only if the angle of incidence is less than or equal to the angle of reception.

To analyze the collecting efficiency of the inner-outer collecting channel, the detecting light reflected from or scattered by the sample tissue 40 may be modeled first, where a typical diffuse reflector is used, and a diffuse luminescent surface is also referred to as a cosine radiator.

Figure 9:
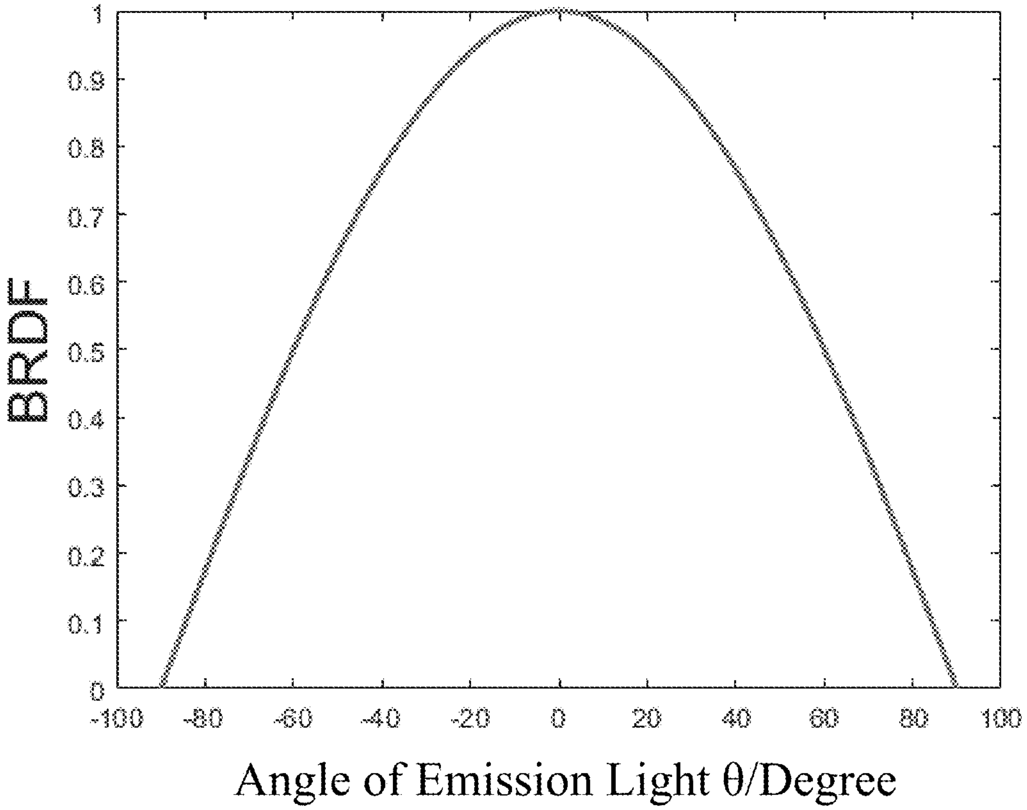
FIG. 9 is a schematic diagram illustrating a Bidirectional Reflectance Distribution Function varying with an emission angle of a diffuse reflector according to some embodiments of the present disclosure.

FIG. 9 is a schematic diagram illustrating the variation of a Bidirectional Reflectance Distribution Function of a diffuse reflector according to some embodiments of the present disclosure. A horizontal axis is the angle of emission light and a vertical axis is a Bidirectional Reflectance Distribution Function (BRDF).

As shown in FIG. 9, a spatial distribution of a luminous intensity of the luminous surface of the diffuse reflector is shown in equation 8:

$$I_\theta = I_N\cos\theta, \quad (8);$$

where $I_N$ is the luminous intensity of the luminous surface of the diffuse reflector in the normal direction, and $I_\theta$ is the luminous intensity of the luminous surface of the diffuse reflector at an arbitrary angle in a direction θ.

After the emission light is irradiated on the diffuse reflector, a portion of the emission light reflected by the diffuse reflector forms a cosine radiant body, the brightness of the cosine radiant body in all directions are same, and an equation determining the luminous flux emitted by the cosine radiant body to a range of a surface aperture three-dimensional angle is shown in equation 9:

$$\emptyset = LdA\int_{\varphi=0}^{\varphi=2\pi}\int_{\theta=0}^{\theta=U}\sin\theta\cos\theta d\theta d\varphi = \pi LdA\sin^2 U, \quad (9);$$

where Ø is a planar aperture stereo angle, U is an aperture angle formed by the illuminated surface of the collecting fiber and the luminous surface of the diffuse reflector.

When the brightness of the object surface is even, an illumination of the image point after an imaging optical system is shown in equation 10:

$$E'_M = \frac{n'^2}{n^2}\tau\pi L\sin^2 U'_M, \quad (10);$$

where $$E'_M$$

is the illuminance at the image point, n' is a refractive index of an image medium, n is a refractive index of an object medium, τ is an optical transmission ratio of the optical system, and $$U'_M$$

is an image aperture angle. For the detecting light within a range of the numerical aperture of the collecting fiber, its illuminance at the illuminated surface is integrated to obtain the collected luminous flux.

Figure 10:
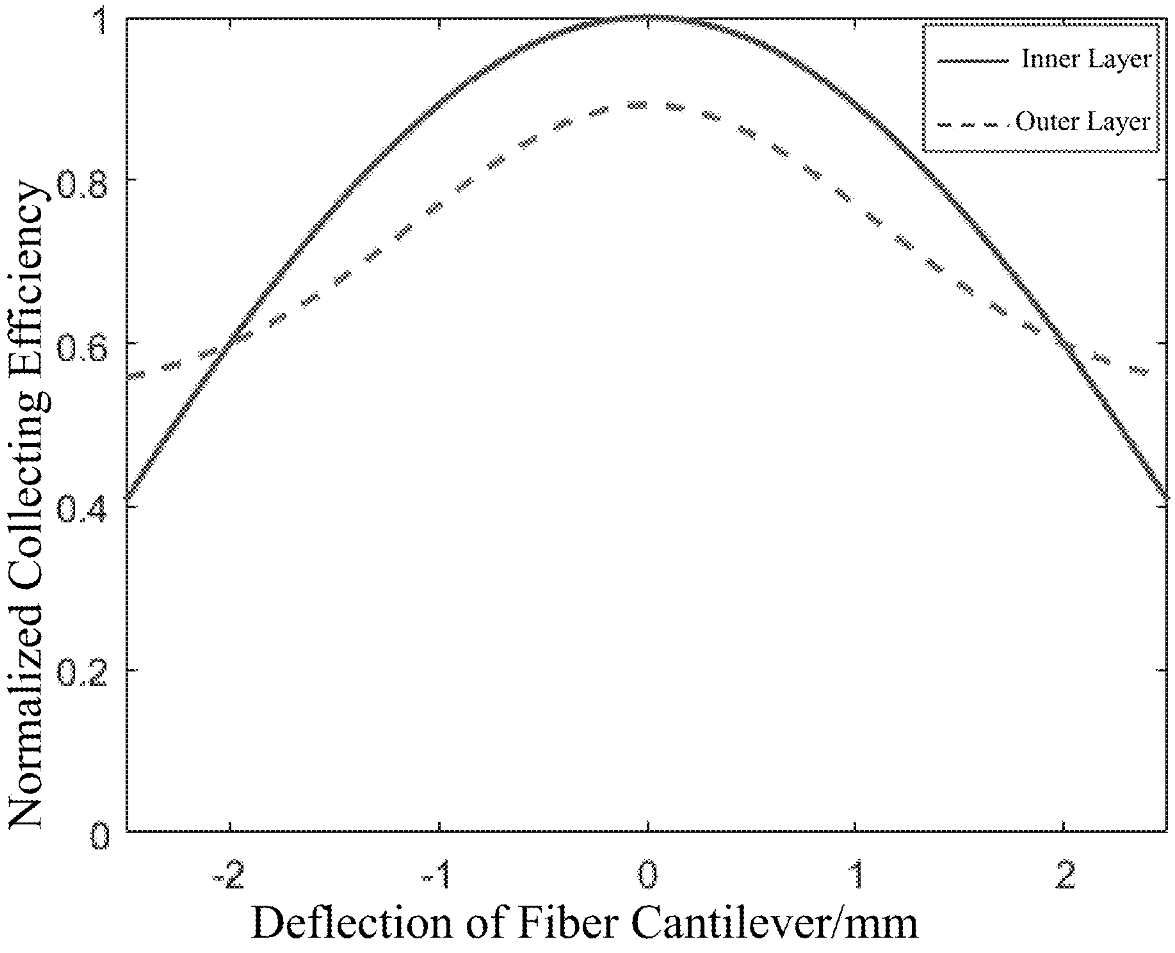
FIG. 10 is a schematic diagram illustrating a variation of a collecting efficiency of an inner-outer layer fiber and an amplitude of a fiber cantilever according to some embodiments of the present disclosure.

For the outer-fiber collecting array 30 (i.e., the outer layer), the collecting efficiency of the detecting light depends only on an area of the illuminated surface of the collecting fibers and the numerical aperture of the collecting fiber, which is relatively determined after the collecting fibers are determined. For example, a plastic fiber with a diameter of 50 um and a numerical aperture of 0.6 is used for the analysis. A calculation simulation is performed according to equation 5, equation 6, and equation 9 to obtain a curve of a variation of the amplitude of the fiber cantilever relative to the collecting efficiency as shown in FIG. 10, FIG. 10 is a schematic diagram illustrating a variation of the collecting efficiency of inner-outer layer fiber and the amplitude of a fiber cantilever according to some embodiments of the present disclosure.

For the inner-layer fiber collecting array 20 (i.e., the inner layer), when the same collecting fiber is used as in the outer-layer fiber collecting array 30 (i.e., the outer layer), a design of the inner-layer fiber collecting array 20 is also limited by parameters such as the deflection angle of the fiber cantilever, the numerical aperture of the single-mode fiber, and the focal length of the lens set 12, which need to be analyzed.

For the fiber cantilever in the scanning, a beam emitted by a terminal thereof at a certain divergence angle forms a spatial stereo angle that is approximately in a conical shape with the principal surface of the object space of the lens set 12. Since the inner-layer fiber collecting array 20 is not able to affect an imaging operation of the scanning illumination optical path, an inner diameter of the inner-layer fiber collecting array 20 should be between a maximum offset of the fiber cantilever and an inner diameter of the sleeve 13. In other words, the inner diameter of the inner-layer fiber collecting array 20 is greater than twice the maximum offset of the fiber cantilever 112*a* and less than an inner diameter of the sleeve, which mathematical expression can be shown in formula 11 as follows:

$$2z_{max} < 2R < D, \quad (11);$$

where $z_{max}$ is the maximum offset of the fiber cantilever 112*a*, R is a radius of the inner-layer fiber collecting array 20, and D is the inner diameter of the sleeve 13. For example, the inner diameter of the sleeve 13 is designed to be 1 mm, the object distance is designed to be 1 mm, the maximum offset of the fiber cantilever is designed to be 0.25 mm, and the inner-layer fiber collecting array 20 is made of a plastic fiber with a diameter of 50 um and a numerical aperture of 0.6. After the parameters of the collecting fiber used in the inner-layer fiber collecting array 20 are determined, the collecting efficiency of the inner-layer fiber collecting array 20 is as high as possible.

The inner-fiber collecting array 20 in the axial position of the sleeve should be located behind the spatial stereo angle formed by the scanning illumination optical path 10, as shown in equation 12:

$$\text{arc}tran\frac{R}{u+L-l} > \alpha, \tag{12;}$$

where R refers to the radius of the inner-layer fiber collecting array 20, u refers to a distance between a distal end of the fiber cantilever 112*a* and the principal surface of the object space of the lens set 12, L refers to the length of the fiber cantilever 112*a*, l refers to a distance between the illuminated surface of the inner-layer fiber collecting array 20 and the principal surface of the object of the lens set 12, and a refers to the deflection angle of the fiber cantilever 112*a*.

Due to a focusing effect of the lens set 12, the closer the detecting light incident into the inner cavity of the endoscope probe is to the focal point, the greater the light energy is, so that to optimize the position of the inner-layer fiber collecting array 20, in conjunction with equation 11 and equation 12, a relationship curve between the non-confocal detection light and the axial position of the inner-layer fiber collecting array 20 is obtained by calculation simulation and comparing with the outer-layer fiber collecting array 30 as shown in FIG. 10.

From the calculation results, it may be seen that the non-confocal light flux rises with the increase of the distance of the inner-layer fiber collecting array 20 from the lens set 12, and the collecting efficiency of the inner-layer fiber collecting array 20 may be greater than the collecting efficiency of the outer-layer fiber collecting array 30 after a certain distance is reached. Therefore, in conjunction with equation 6, equation 9, and equation 10, a radius of the inner-layer fiber collecting array 20 is set to 0.35 mm, and an axial position is at 0.6 mm from the lens set. Therefore, in some embodiments, the axial position of the illuminated surface of the inner-layer fiber collecting array 20 inside the sleeve 13 may be located at the focal point of the lens set 12 to collect as much of the detecting light incident inside the sleeve 13 as possible.

Figure 11:
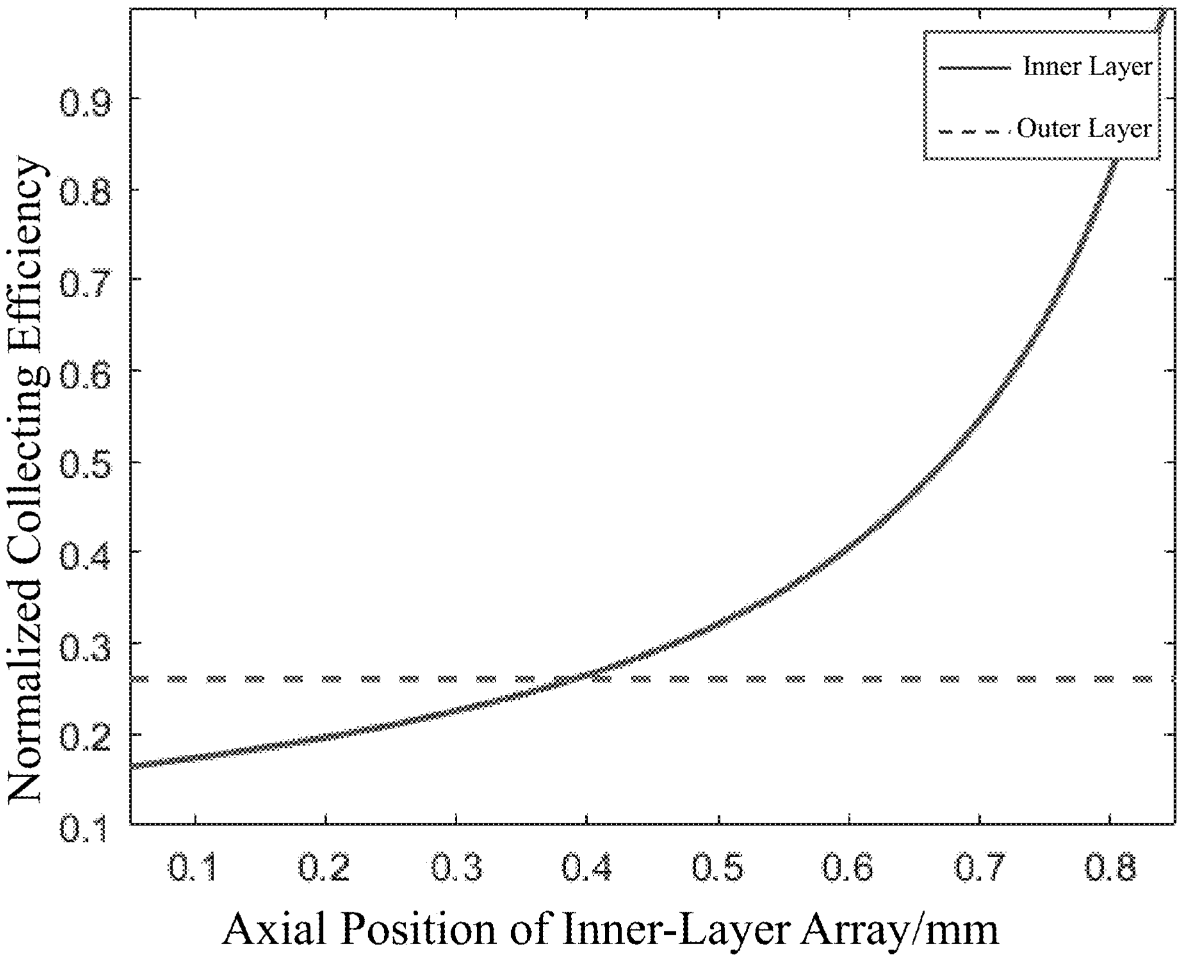
FIG. 11 is a schematic diagram illustrating a relationship between a collecting efficiency of an inner-outer collecting channel and an axial position of the inner-layer collecting channel according to some embodiments of the present disclosure.

FIG. 11 is a schematic diagram illustrating a relationship between the collecting efficiency of an inner-outer collecting channel and an axial position of the inner-layer collecting channel according to some embodiments of the present disclosure.

As shown in FIG. 11, relative to the outer-layer fiber collecting array 30, the setting of the inner-layer fiber collecting array 20 enhances under different deflection angles of the fiber cantilever relative to the collection efficiency of an overall endoscope probe to different degrees, and at the highest, a relative collecting efficiency is improved by 113.6%.

For the scanning fiber endoscope, the optical intensity signal received by the detection device is a very important indicator, and the strength of the collected light energy in the present disclosure depends on an area of the illuminated surface of the outer-layer fiber collecting array 30 and the inner-layer fiber collecting array 20, the relative aperture angles of the light-emitting surface and the light-receiving surface and the numerical aperture of the collecting fiber used, which are essentially determined by the parameters of the outer-layer fiber collecting array 30 and the inner-layer fiber collecting array 20 (e.g., the diameter, the count, the position, and the material, etc.). Therefore, by setting various parameters of the outer-layer fiber collecting array 30 and the inner-layer fiber collecting array 20, a higher light energy is obtained relative to a conventional scanning fiber endoscope, and the imaging quality is improved.

Figure 12:
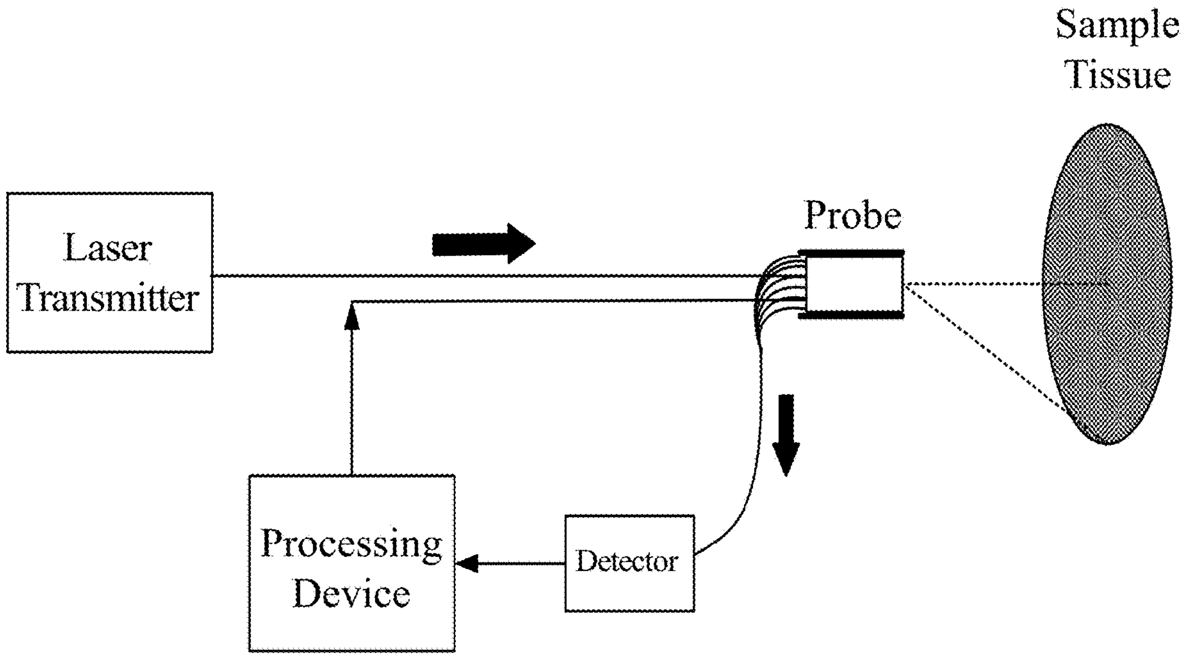
FIG. 12 is a schematic diagram illustrating a principle structure of a scanning fiber endoscope according to some embodiments of the present disclosure.

FIG. 12 is a schematic diagram illustrating a principle structure of a scanning fiber endoscope according to some embodiments of the present disclosure.

As shown in FIG. 12, in some embodiments, the scanning fiber endoscope includes a laser transmitter, a scanning fiber endoscope probe, a detector, and a processing unit.

The laser transmitter synthesizes a three-color laser into a co-axial beam and transmits the coaxial beam to the sample tissue through the single-mode fiber in the scanning fiber endoscope probe.

The scanning fiber endoscope probe may refer to a scanning fiber endoscope probe in any one of the foregoing embodiments.

The detector may refer to the photoelectric detector covered in any one of the foregoing embodiments. The detector converts an optical intensity signal into a time-sequenced optical intensity electrical signal.

The processing device processes a time-sequenced optical intensity signal, a control drive signal of the scanning fiber endoscope probe through an algorithm to obtain an image of the sample tissue.

In some embodiments, the scanning fiber endoscope probe may include a scanning illumination optical path and an inner-layer fiber collecting channel. The scanning illumination optical path is configured to scan the laser emitted by the light source to create the optical spot on the surface of a sample tissue and to create a field of view. The inner-layer fiber collecting channel is configured to collect and transmit a portion of detecting light scattered from or reflected by the sample tissue through the lens set to perform the imaging by the photoelectric detector. In some embodiments, the scanning illumination optical path may drive the single-mode fiber to scan through the microelectromechanical device. In some embodiments, the microelectromechanical drive may be a motor actuator, an electrothermal actuator, an electromagnetic actuator, a piezoelectric actuator, or other forms of actuator. The piezoelectric actuator may be a piezoelectric ceramic tube.

In some embodiments, the scanning fiber endoscope probe may further include the outer-fiber collecting array. The outer-fiber collecting array is a tubular fiber array formed by disposing a plurality of collecting fibers at the periphery of the cavity of the scanning illumination optical path and is configured to collect and transmit the portion of the detecting light scattered from or reflected by the sample tissue back to the exterior of the scanning illumination optical path to perform the imaging by the photoelectric detector.

In some embodiments, the scanning illumination optical path may include a vibrating component, a lens set, a sleeve, and a fixture. The vibrating component is disposed on the proximal end of the cavity of the sleeve and at located at a proximal end of the lens set. The inner-layer fiber collecting array is located at the proximal end of the lens set and is provided on the outer side of the vibrating component, the inner-layer fiber collecting array is a tubular fiber array surrounded by a plurality of collecting fibers; the fixture fixes the vibrating component within the sleeve and fixes the inner-layer fiber collecting array between the sleeve and the vibrating component, and the inner-layer fiber collecting array is configured to collect a portion of detecting light entering into the cavity of the scanning endoscope probe through the lens set.

In some embodiments, the inner-layer fiber collecting array may include one or two layers, and/or, the outer-layer fiber collecting array may include one or two layers. For example, the inner-layer fiber collecting array includes one layer and the outer-layer fiber collecting array includes two layers. As another example, the inner-layer fiber collecting array includes two layers and the outer-layer fiber collecting array includes one layer. As another example, the inner-layer fiber collecting array includes two layers and the outer-layer fiber collecting array includes two layers.

The various technical features of the above embodiments may be combined in any combination, and all possible combinations of the various technical features of the above embodiments have not been described for the sake of conciseness of description; however, as long as there is no contradiction in the combinations of these technical features, they should be considered to be within the scope of the present disclosure.

The above embodiments express only several embodiments of the present disclosure, which are described in a more specific and detailed manner, but are not to be construed as a limitation of the patent scope of the invention. It should be pointed out that, for those skilled in the art, several deformations and improvements can be made without departing from the conception of the present disclosure, which all fall within the scope of protection of the present disclosure. Therefore, the scope of protection of the present disclosure shall be subject to the appended claims.

What is claimed is:

1. A scanning fiber endoscope probe, comprising: a scanning illumination optical path, an outer-layer fiber collecting array, and an inner-layer fiber collecting array, wherein the scanning illumination optical path includes a lens set, a vibrating component, and a fixture, wherein the scanning illumination optical path is configured to scan laser emitted by a light source to form an optical spot on a surface of a sample tissue and to form a field of view;

the vibrating component is disposed within a cavity of a sleeve and at a proximal end of the lens set, wherein the proximal end of the lens set refers to a side closer to the lens set; and the fixture fixes the vibrating component within the sleeve; and the vibrating component includes a piezoelectric ceramic tube and a single-mode fiber;

wherein the single-mode fiber is fixedly disposed on the piezoelectric ceramic tube, and protrudes and extends a fiber of a preset length at a distal end of the piezoelectric ceramic tube to form a fiber cantilever;

the piezoelectric ceramic tube is configured to drive the fiber cantilever to vibrate in a resonance mode for scanning under a drive of an alternating voltage of a preset frequency;

the lens set disposed at a side close to a distal end of the fiber cantilever is configured to focus dispersed light emitted by the single-mode fiber and image on the sample tissue;

a distance between an end of the fiber cantilever and a principal surface of an object space of the lens set matches an angle of field of view and a size of an optical spot of a circular field of view; and the piezoelectric ceramic tube and the lens set are fixedly disposed in the sleeve, wherein the piezoelectric ceramic tube is fixedly disposed in the sleeve;

the inner-layer fiber collecting array is configured to collect and transmit a portion of detecting light scattered from or reflected by the sample tissue through the lens set to perform an imaging by a photoelectric detector, wherein the inner-layer fiber collecting array is located on a side of the lens set that is away from the sample tissue along an axial direction of the lens set; and the outer-layer fiber collecting array is a tubular fiber array formed by disposing a plurality of collecting fibers at a periphery of a cavity of the scanning illumination optical path and is configured to collect and transmit a portion of the detecting light scattered from or reflected by the sample tissue back to an exterior of the scanning illumination optical path to perform an imaging on the photoelectric detector.

2. The scanning fiber endoscope probe of claim 1, wherein the scanning illumination optical path further includes the sleeve, the inner-layer fiber collecting array is fixed within the cavity of the sleeve.

3. The scanning fiber endoscope probe of claim 1, wherein the inner-layer fiber collecting array is located at the proximal end of the lens set and is disposed on an outer side of the vibrating component, and the fixture installs the inner-layer fiber collecting array between the sleeve and the vibrating component.

4. The scanning fiber endoscope probe of claim 1, wherein the inner-layer fiber collecting array is located at the proximal end of the lens set and is disposed on an outer side of the vibrating component, and the inner-layer fiber collecting array is disposed on an outer side of the fixture.

5. The scanning fiber endoscope probe of claim 1, wherein the fixture is a circular ring with an opening, one end of the opening of the circular ring is provided with a first buckle, another end of the opening of the circular ring is provided with a first slot, the first buckle is inserted into the first slot, and then the first buckle and the first slot are fixed relative to each other by using a first fixing member.

6. The scanning fiber endoscope probe of claim 1, wherein the fixture is divided into a first half-circular ring and a second half-circular ring, each of two ends of the first half-circular ring is provided with a second buckle, respectively, each of two ends of the second half-circular ring is provided with a second slot, respectively, the first buckle is inserted into the second slot, and then the second buckle and the second slot are fixed relative to each other by using a second fixing member.

7. The scanning fiber endoscope probe of claim 1, wherein the fixture includes a fixture body, and a fixture body includes:

a vibrating component fixing hole, wherein the vibrating component fixing hole is coaxial with a center axis of the fixture body; and at least two inner-layer fiber fixing holes, wherein the at least two inner-layer fiber fixing holes are distributed evenly relative to a circumference of the center axis of the fixture body, and each collecting fiber of the inner-layer fiber array is disposed on the at least two inner-layer fiber fixing holes, respectively.

8. The scanning fiber endoscope probe of claim 1, wherein an inner diameter of the inner-layer fiber collecting array and an axial position inside the sleeve are determined based on a spatial stereo angle formed by the fiber cantilever in the scanning illumination optical path during a vibrating process, thereby improving a collecting efficiency of the inner-layer fiber collecting array without interfering with the scanning illumination optical path.

9. The scanning fiber endoscope probe of claim 8, wherein an inner diameter of the inner-layer fiber collecting array is greater than twice a maximum offset of the fiber cantilever and less than an inner diameter of the sleeve, or a distance between an illuminated surface of the inner-layer fiber collecting array and the principal surface of the object space of the lens set is less than a distance between the distal end of the fiber cantilever and the principal surface of the object space of the lens set.

10. The scanning fiber endoscope probe of claim 8, wherein an axial position of the inner-layer fiber collecting array inside the sleeve satisfies a constraint relationship:

$$\arctan\frac{R}{u+L-l} > a;$$

where R refers to a radius of the inner-layer fiber collecting array, u refers to a distance between the distal end of the fiber cantilever and the principal surface of the object space of the lens set, L refers to a length of the fiber cantilever, l refers to a distance between an illuminated surface of the inner-layer fiber collecting array and the principal surface of the object space of the lens set, the illuminated surface is a surface that receives the detecting light on the inner-layer fiber collecting array, and a refers to a deflection angle of the fiber cantilever.

11. The scanning fiber endoscope probe of claim 1, wherein an axial position of an illuminated surface of the inner-layer fiber collecting array inside the sleeve is located at a focal point of the lens set.

12. The scanning fiber endoscope probe of claim 1, wherein in the scanning illumination optical path, a diameter of the fiber cantilever of the single-mode fiber after a corrosion process is less than a standard diameter of the single-mode fiber.

13. The scanning fiber endoscope probe of claim 1, wherein a maximum outer diameter of the scanning fiber endoscope probe is less than or equal to 1.5 mm, a length of the fiber cantilever is within a range of 2 mm to 4 mm, an imaging frame rate of the photoelectric detector is within a range of 15 fps to 25 fps, and a scanning amplitude of the fiber cantilever is within a range of 0.5 mm to 0.8 mm.

14. The scanning fiber endoscope probe of claim 1, wherein the inner-layer fiber collecting array includes one or two layers, and/or, the outer-layer fiber collecting array includes one or two layers.

15. The scanning fiber endoscope probe of claim 1, wherein the outer-layer fiber collecting array and the inner-layer fiber collecting array form an inner-outer collecting channel, one or more fibers of the inner-outer collecting channel are evenly distributed on an inner circumference and an outer circumference of the inner-outer collecting channel, the inner-outer collecting channel is configured to collect the portion of the detecting light scattered from or reflected by the sample tissue, and a field of view of the inner-outer collecting channel is greater than a field of view of the scanning illumination optical path.

16. The scanning fiber endoscope probe of claim 1, wherein the outer-layer fiber collecting array is located at a periphery of the lens set along a radial direction of the lens set.

17. A scanning fiber endoscope, comprising a scanning fiber endoscope probe and a photoelectric detector, the scanning fiber endoscope probe including: a scanning illumination optical path, an inner-layer fiber collecting array, and an outer-layer fiber collecting array; wherein the scanning illumination optical path includes a lens set, a vibrating component, a sleeve and a fixture, wherein the scanning illumination optical path is configured to scan laser emitted by a light source to form an optical spot on a surface of a sample tissue and to form a field of view;

the vibrating component is located in an innermost portion of a cavity of the sleeve and is located at a proximal end of the lens set; and the fixture fixes the vibrating component within the sleeve; and the vibrating component includes a piezoelectric ceramic tube and a single-mode fiber; wherein the single-mode fiber is fixedly disposed on the piezoelectric ceramic tube, and protrudes and extends a fiber of a preset length at a distal end of the piezoelectric ceramic tube to form a fiber cantilever;

the piezoelectric ceramic tube is configured to drive the fiber cantilever to vibrate in a resonance mode for scanning under a drive of an alternating voltage of a preset frequency;

the lens set disposed at a side close to a distal end of the fiber cantilever is configured to focus dispersed light emitted by the single-mode fiber and image on the sample tissue;

a distance between an end of the fiber cantilever and a principal surface of an object space of the lens set matches an angle of field of view and a size of an optical spot of a circular field of view; and the piezoelectric ceramic tube and the lens set are fixedly disposed in the sleeve, wherein the piezoelectric ceramic tube is fixedly disposed in the sleeve;

the inner-layer fiber collecting array is configured to collect a detecting light scattered from or reflected by the sample tissue and collected through the lens set, wherein the inner-layer fiber collecting array is located on a side of the lens set that is away from the sample tissue along an axial direction of the lens set;

the outer-layer fiber collecting array is a tubular fiber array formed by disposing a plurality of collecting fibers at a periphery of a cavity of the scanning illumination optical path and is configured to collect and transmit a portion of the detecting light scattered from or reflected by the sample tissue back to an exterior of the scanning illumination optical path to perform an imaging on the photoelectric detector; and the photoelectric detector collects the detecting light collected by the inner-layer fiber collecting array and performs an imaging on the detecting light.

18. The scanning fiber endoscope of claim 17, the inner-layer fiber collecting array is located at a proximal end of the lens set and is disposed at an outer side of the vibrating component, and the inner-layer fiber collecting array is a tubular fiber array surrounded by a plurality of fibers;

the fixture fixes the inner-layer fiber collecting array between the sleeve and the vibrating component; and the inner-layer fiber collecting array is configured to collect a portion of detecting light entering a cavity of the probe through the lens set.

* * * * *